(12) United States Patent
Dobson et al.

(10) Patent No.: US 7,698,070 B2
(45) Date of Patent: Apr. 13, 2010

(54) METHOD AND APPARATUS FOR ASSESSING POLYPEPTIDE AGGREGATION

(75) Inventors: Christopher Dobson, Cambridgeshire (GB); Fabrizio Chiti, Scandicci (IT); Jesus Zurdo, Cambridgeshire (GB); Kateri Hayashi DuBay, Berkeley, CA (US); Michele Vendruscolo, Cambridgeshire (GB)

(73) Assignee: Cambridge University Technical Services Ltd. (GB)

( * ) Notice: Subject to any disclaimer, the term of this patent is extended or adjusted under 35 U.S.C. 154(b) by 0 days.

(21) Appl. No.: 11/417,525

(22) Filed: May 4, 2006

(65) Prior Publication Data

US 2006/0271306 A1 Nov. 30, 2006

Related U.S. Application Data

(63) Continuation of application No. PCT/GB2004/050015, filed on Oct. 1, 2004.

(51) Int. Cl.
G06F 17/11 (2006.01)
G06F 17/50 (2006.01)
G06F 19/00 (2006.01)

(52) U.S. Cl. ............... 702/19; 702/23; 703/11
(58) Field of Classification Search .......... 702/19; 703/11
See application file for complete search history.

(56) References Cited

U.S. PATENT DOCUMENTS

| 6,188,965 | B1 | 2/2001 | Mayo et al. |
| 6,269,312 | B1 | 7/2001 | Mayo et al. |
| 6,708,120 | B1 | 3/2004 | Mayo et al. |
| 7,379,824 | B2 | 5/2008 | Dobson et al. |
| 2006/0025977 | A1 | 2/2006 | Dobson et al. |
| 2008/0183455 | A1 | 7/2008 | Dobson et al. |
| 2008/0262742 | A1 | 10/2008 | Dobson et al. |

FOREIGN PATENT DOCUMENTS

| EP | 1255209 A2 | 11/2002 |
| WO | WO-00/17328 A2 | 3/2000 |
| WO | WO-02/42321 A2 | 5/2002 |
| WO | WO-2004/066168 A1 | 8/2004 |

OTHER PUBLICATIONS

Chiti et al. PNAS, Dec. 10, 2002, vol. 99, Suppl. 4, 16419-16426.*
Broome et al. Journal of Molecular Biology, 296, 4, Mar. 3, 2000, pp. 961-968.*

(Continued)

Primary Examiner—Michael Borin
(74) Attorney, Agent, or Firm—Schwegman, Lundberg & Woessner, P.A.

(57) ABSTRACT

A method of determining aggregation rate data predicting an aggregation rate of a polypeptide defined by an amino acid sequence, the method comprising determining a hydrophobicity value, a charge value, and at least one shape propensity value for said sequence; identifying one or more aggregation-influencing patterns within said sequence; determining a pattern value for the sequence responsive to said identifying; and determining said aggregation rate data by determining a weighted combination of said hydrophobicity value, said charge value, said at least one shape propensity value, said pattern value and at least one factor extrinsic to said amino acid sequence.

10 Claims, 13 Drawing Sheets

OTHER PUBLICATIONS

Qamar et al. J. Biochem, 1993, vol. 114, No. 6 786-79.*
Avbel J, F., Journal of Molecular Biology, 300, 5, 2000 1335-135.*
Chiti et al. Nature Structural Biology 9, 137-143 (2002).*
"U.S. Appl. No. 11/184,548, Non-Final Office Action mailed Jul. 9, 2007", 9 pgs.
"U.S. Appl. No. 11/184,548, Notice of Allowance mailed Jan. 29, 2008", 4 pgs.
"U.S. Appl. No. 11/184,548,Supplemental Notice of Allowance mailed Mar. 12, 2008", 4 pgs.
International Application Serial No. PCT/GB2004/000089, International Search Report mailed Jun. 23, 2004, 5 pgs.
Avbelj, F., "Amino Acid Conformational Preferences and Solvation of Polar Backbone Atoms in Peptides and Proteins", *Journal of Molecular Biology*, 300(5), (2000), 1335-1359.
Avbelj, F., et al., "Role of Main-Chain Electrostatics, Hydrophobic Effect and Side-Chain Conformational Entropy in Determining the Secondary Structure of Proteins", *Journal of Molecular Biology*, 279(3), (1998),665-684.
López De La Paz, M. L., et al., "*De novo* Designed Peptide-Based Amyloid Fibrils", *Proc Natl Acad Sci USA*., 99(25), (2002), 16052-16057.
Qamar, S., et al., "Probing the Determinations of Protein Solubility with Amino Acid Modification", *Journal of Biochemistry*, 114(6), (Abstract Only), (1993), 1 pg.
Siepen, J. A., et al., "The fibril_one On-line Database: Mutations, Experimental Conditions, and Trends Associated With Amyloid Fibril Formation", *Protein Science*, 11, (Jul. 2002), 1862-1866.

* cited by examiner

METHOD AND APPARATUS FOR ASSESSING POLYPEPTIDE AGGREGATION

RELATED APPLICATIONS

This application is a continuation under 35 U.S.C. 111(a) of PCT/GB2004/050015, filed Oct. 1, 2004 and published as WO 2005/045442 A1, filed May 19, 2005, which claimed priority under 35 U.S.C. 119 to United Kingdom Application No. 0325817.5, filed Nov. 5, 2003, which applications and publication are incorporated herein by reference and made a part hereof.

TECHNICAL FIELD

This invention relates to methods, apparatus and computer programs for determining rates of aggregation of polypeptides, and to polypeptides designed using these methods and apparatus.

BACKGROUND

An understanding of the propensities of specific polypeptides to aggregate is of crucial importance for elucidating the molecular basis of protein deposition diseases, such as Alzheimer's and other amyloid diseases, and for understanding the mechanisms of action of the mutations associated with hereditary forms of such diseases.

In each of the various pathological conditions associated with protein and peptide deposition, a specific peptide or protein that is normally soluble is deposited, either intact or in fragmented form, into insoluble aggregates that accumulate in one or more type(s) of tissue. Numerous mutations have been found to be associated with familial forms of protein deposition diseases and more than 100 have been shown directly to involve the sequence of the peptide or protein responsible for aggregation (Siepen and Westhead, 2002). Many of these mutations have been identified over the past 5 years, and the number is expected to increase dramatically in the near future. Investigation of the mechanisms by which natural mutations result in pathological behaviour has proved to be of fundamental importance for exploring the molecular basis of the underlying disease, even in those cases where they are sporadic rather than familial in origin (Selkoe, 2001; Volles & Lansbury, 2002).

The ability to form highly organised aggregates having common structural characteristics, such as amyloid, has been found to be a generic property of polypeptides, regardless of sequence or structural similarity, and not simply a feature of small numbers of proteins associated with recognised pathological conditions (Dobson, 2001).

In the native state, hydrophobic residues are usually embedded within the core of a protein, thus the opportunity for these residues to interact is limited. However, proteins are dynamic and an equilibrium exists between the stable and folded conformation, and destabilised, partially or fully unfolded states. The free energy value ($\Delta G$, kJ mol$^{-1}$) for a protein provides an indication of the stability of the protein. Aggregation occurs when proteins in their native state denature; as the protein unfolds, intramolecular bonds are broken, allowing the polypeptide main chain (backbone) and hydrophobic side chains to be exposed. Hydrogen bonds and other interactions can then form between the partially or fully denatured protein molecules, resulting in intermolecular associations and aggregate formation.

In some instances, it may be desirable to form aggregates, in particular fibrils, for example for use as plastic materials, in electronics, as conductors, for catalysis or as a slow release form of the polypeptide, or where polypeptide fibrils are to be spun into a polypeptide "yarn" for various applications; for example, as described in published patent applications WO0017328 (Dobson) and WO0242321 (Dobson & McPhee).

However, in other circumstances the formation of aggregates is disadvantageous, for example, when it is desired to use a polypeptide at concentrations or under conditions desirable for physiological activity, therapeutic administration or industrial application. In particular, the use of bioactive peptides and proteins as pharmaceutical agents is limited where the peptide or protein tends to form aggregates during manufacture, processing, storage or following administration. These issues are widely recognised in the biotechnological and pharmaceutical industry and constitute a major problem and economic burden, that can be difficult to overcome and may require the use of sophisticated expression and refolding techniques, the development of specific formulations, stabilising agents and excipients, cold chain delivery, or immediate reconstitution before use. Almost all known polypeptide therapeutic products present these problems, e.g. insulin, interferon-$\gamma$, BMPs, calcitonin, glucagon, antibodies.

Various factors are known to affect the tendency of a polypeptide to aggregate. Some of these factors are local to amino acid residues, other factors are global and can affect the entire protein. For example, when mutations are made in a polypeptide, local factors in the region of the mutation such as increased hydrophobicity, or tendency to convert from $\alpha$-helix to $\beta$-sheet conformation, result in a higher rate of aggregation than that of the wild type (non-mutant) protein. "Global" or overall changes due to mutations can also affect the rate of aggregation; for example, a change in net charge of the mutant polypeptide bringing it closer to neutral results in an increased tendency of a polypeptide to aggregate. Mutations that destabilise the native state of the polypeptide also result in facilitated aggregation.

A detailed mutational study on a model protein, muscle acylphosphatase (AcP), demonstrated that the rate of aggregation for an ensemble of partially denatured conformations can be followed readily for AcP using a variety of spectroscopic probes. The rate of aggregation was determined for over 50 mutational variants of this protein (Chiti et al., 2002a; 2002b: Chiti, F., Taddei, N., Baroni, F., Capanni, C., Stefani, M., Ramponi, G. & Dobson, C. M. Kinetic partitioning of protein folding and aggregation. *Nature Struct. Biol.* 9, 137-143 (2002a); Chiti, F., Calamai, M., Taddei, N., Stefani, M. Ramponi, G. & Dobson, C. M. Studies of the aggregation of mutant proteins in vitro provide insights into the genetics of amyloid diseases. *Proc. Natl. Acad. Sci. USA*, 99: 16419-16426 (2002b)). Many of these mutations, particularly those involving residues 16-31 and 87-98, were found to perturb the aggregation rate of AcP very significantly (Chiti et al., 2002a; 2002b). Chiti (2002a) concluded that the measured changes in aggregation rate upon mutation positively correlated with changes in the hydrophobicity and $\beta$-sheet propensity of the regions of the protein in which the mutations are located. Chiti (2002b) examined AcP mutations that altered the charge state of the AcP protein without affecting significantly the hydrophobicity or secondary structure propensitities of the polypeptide chain. An inverse correlation was reported between the rate of aggregation of protein variants under denaturing conditions and the overall net charge of the protein.

The factors that affect the rate of aggregation of a protein are diverse. When amino acid substitutions are made in a protein, several factors are involved to different extents. A single mutation can increase the net charge, thereby disfavouring aggregation (for example, the replacement of Ala for Asp in a positively charged protein). Nevertheless, the same mutation can increase hydrophobicity, thereby bringing an accelerating contribution to the aggregation rate. Finally, the same mutation also changes the α-helical and β-sheet propensities of the polypeptide chain, introducing other factors. The relationship between these factors and their relative importance to aggregation (solubility) are not well characterised.

Thus, it has not been possible to predict accurately the tendency of a protein to form insoluble and ordered aggregates, such as amyloid fibrils, nor to predict or calculate the effect of specific amino acid modifications, such as replacements, on aggregation/solubility. The inability to make such predictions or calculations constitutes a problem in the design and/or handling of polypeptides, whether in vivo or in vitro.

The ability to predict polypeptide aggregation is of crucial importance in elucidating the pathogenic effect of the large numbers of mutations associated with protein deposition diseases. Establishment of general principles in aggregation would make it possible to use statistical methods to analyse the relationships between mutation, aggregation and disease. An understanding of the propensities of specific proteins to aggregate would allow the establishment of criteria to modify rationally the aggregational properties of natural or designed peptides and proteins for industrial processes, research purposes, medical treatment or biotechnological application. Furthermore, methods of the invention may be used to identify or design polypeptide sequences with a reduced aggregation propensity, re-designed polypeptides could be administered by methods such as gene therapy to treat certain disorders, particularly those associated with protein aggregation. The ability to identify or design polypeptides with specific aggregation properties will be important for development and manufacture of polypeptides for applications in the material and device areas, such as those described in WO0017328 (Dobson) and WO0242321 (Dobson & McPhee).

It would therefore be useful to be able to determine which parts of an amino acid sequence promote aggregation, to be able to determine whether a particular polypeptide is likely to form insoluble aggregates, and to be able to predict the effect that a particular modification or modifications of amino acid sequence will have on the aggregation/solubility properties of a polypeptide.

DETAILED DESCRIPTION OF THE INVENTION

In a first aspect the invention provides a method for identifying a part of an amino acid sequence which is predicted to promote aggregation of a polypeptide defined by said sequence, the method comprising: determining aggregation propensities for a plurality of parts of said sequence; and comparing said aggregation propensities to determine one or more parts of said sequence which are predicted to promote aggregation.

Embodiments of this method allow "profiling" of an amino acid sequence to determine those regions which are likely to promote aggregation. As with the "absolute" aggregation rate determination methods described below, one or more extrinsic factors (ie. factor extrinsic to the amino acid sequence) such as salt concentration, protein concentration, pH, temperature and the like may also be taken into account in the determination of parts of the sequence predicted to promote aggregation or "profiling" of the sequence. This may be done, for example, by adding an additional extrinsic-factor dependent term in the aggregation propensity prediction model(s) described later.

Preferably the determining comprises determining, for each of a plurality of amino acids of said sequence, a hydrophobicity value, an α-helix and/or β-sheet propensity value, a charge value, and a pattern value representing a pattern of hydrophilic and/or hydrophobic amino acids in the vicinity of each said amino acid, multiplying each of said values by a scaling factor, and summing said scaled values to determine said aggregation propensities. The pattern may comprise a pattern of alternating hydrophilic and hydrophobic amino acids, preferably with a length of at least five amino acids.

The method may further comprise modifying said amino acid sequence and repeating said relative aggregation propensity determining to identify one or more parts of said sequence which are predicted to promote aggregation, in particular for each of a plurality of positions in said amino acid sequence, selecting each of a plurality of alternative amino acids for said repeated relative propensity determining. The method may include comparing said repeatedly determined aggregation propensities to identify one or more parts of said sequence which are predicted to promote aggregation.

The invention further provides a method for designing a polypeptide including predicting an aggregation rate for one or more polypeptides using the above method.

The invention further provides methods for making a polypeptide, in particular a method for making a polypeptide designed by the above method; and a method for making a polypeptide including predicting an aggregation rate for one or more polypeptides. Also provided is a polypeptide obtainable or obtained by a method for making a polypeptide according to the invention.

The invention also provides computer program code to, when running, identify a part of an amino acid sequence which is predicted to promote aggregation of a polypeptide associated with the sequence, the code comprising code to: determine a relative aggregation propensities for a plurality of parts of said sequence; and compare said relative aggregate propensities to determine one or more parts of said sequence which are predicted to promote aggregation.

In a related aspect the invention provides a computer system for identifying a part of an amino acid sequence which is predicted to promote aggregation of a polypeptide associated with the sequence, the computer system comprising: a data store for storing for each of a plurality of amino acids of said sequence, a hydrophobicity value, an α-helix and/or β-sheet propensity value and a charge value, a program store storing processor implementable code; and a processor, coupled to said program store and to said data store for implementing said stored code, the code comprising code for controlling the processor to: input said amino acid sequence; read, for each of a plurality of amino acids of said sequence, a said hydrophobicity value, a said α-helix and/or β-sheet propensity value, and a said charge value, from said data store; determine relative aggregation propensity data for a plurality of parts of said sequence from said hydrophobicity, α-helix and/or β-sheet propensity, and charge values and from a pattern value dependent upon a pattern of hydrophilic and/or hydrophobic amino acids in said sequence; and output said relative aggregation propensity data for identifying a part of said sequence which is predicted to promote aggregation of a polypeptide associated with the sequence.

In another aspect the invention provides a method of determining aggregation rate data predicting an aggregation rate of a polypeptide defined by an amino acid sequence, the method comprising: determining a hydrophobicity value, a charge value, and at least one shape propensity value for said sequence; identifying one or more aggregation-influencing patterns within said sequence; determining a pattern value for the sequence responsive to said identifying; and determining said aggregation rate data by determining a weighted combination of said hydrophobicity value, said charge value, said at least one shape propensity value, said pattern value and at least one factor extrinsic to said amino acid sequence.

Preferably the aggregation rate data predicts an aggregation rate of said polypeptide in a solution, and the at least one extrinsic factor comprises a factor relating to the solution, for example one or more factors selected from a pH value of said solution, an ionic strength of said solution and a measure of a concentration of said polypeptide in said solution. Additional factors which may be employed include temperature, viscosity, dielectric constant and, potentially, a factor or adjustment dependent upon whether the solution is stirred.

The at least one shape propensity value preferably comprises an α-helix propensity value and a β-sheet propensity value. Preferably the determining of the hydrophobicity, charge and shape propensity values of the sequence comprises summing hydrophobicity, charge and shape propensity values for each of a plurality of amino acids of the sequence. Preferably the aggregation rate comprises a logarithm aggregation rate.

The pattern may include a pattern of alternating hydrophobic and hydrophilic amino acids, preferably having a length of five or more amino acids. However additional or alternative patterns such as a pattern of three or more consecutive hydrophobic residues may be employed. As well as patterns thought to promote aggregation, the aggregation rate prediction may be responsive to the identification of aggregation inhibiting patterns within the sequence such as consequtive charges, prolines and the like.

The invention further provides a method for designing a polypeptide, said designing method comprising a method according to the invention. The invention further provides a method for synthesizing a polypeptide comprising designing a polypeptide using a designing method of the invention and synthesising a polypeptide according to said design. A polypeptide obtainable or obtained using a synthesizing method of the invention is also provided.

The invention further provides a polypeptide obtainable or obtained by determining aggregation rate data predicting an aggregation rate of a polypeptide defined by an amino acid sequence and synthesizing a polypeptide with said amino acid sequence. For example, the above methods can be used to predict an aggregation property for a polypeptide (or for many polypeptides, then selecting one or more), and then a polypeptide or polypeptides with the defined amino acid sequence(s) can be synthesised. Synthesis of polypeptides may be performed, for example, by chemical synthesis, or by using molecular biology methods. Synthesis of a polypeptide or polypeptides can be by an automated method.

The term polypeptide as used herein encompasses proteins and peptides.

Using the methods according to embodiments of the invention, the rates of aggregation of polypeptides can be rationalised and predicted to a remarkable extent on the basis of simple physical principles: the effects that the modifications have on the fundamental parameters of hydrophobicity and secondary structure propensity at the site of modification, and on charge of the molecule as a whole. Based on these methods, modified (e.g. mutant) polypeptides can be designed that are more or less liable to aggregate (that have a lesser or greater solubility), or that have a propensity to aggregate within a desired range. Thus it is possible to assess the effects that various amino acid modifications will have on the properties of a polypeptide without having to make modified polypeptides and measure experimentally the effect of the changes. Design of massive numbers of modified polypeptides is potentially feasible. This is important because modifications can be selected also to fulfill other criteria or restrictions, such as protein stability, function etc.

A consensus hydrophobicity scale can be used to assign a hydrophobicity value for each amino acid. Different hydrophobicity scales may be used for different pH values, for example, scales described in Cowan, R. & Whittaker, R. G. (1990) Peptide Research 3: 75-80) may be used to calculate the hydrophobicity of polypeptides at low pH. An averaged hydrophobicity scale can be used, which can be obtained in by using a combination of scales, such as those available in the literature (e.g. Fauchere J.-L & Pliska V. E. (1983) Eur. J. Med. Chem. 18: 369-375; Kyte J., Doolittle R. F. (1982) J. Mol. Biol. 157: 105-132). In a preferred embodiment, the hydrophobicity value for each amino acid is assigned using the values given in Table 1 for hydrophobicity of the 20 amino acid residues at neutral pH based on the partition coefficients from water to octanol; the data are from column 6 of Table 4.8 in Creighton (1993) (Creighton, T. E. In *Proteins. Structure and molecular properties. Second edition*. W. H. Freeman & Company (New York, 1993), p. 154.).

Predicted α-helical propensities can be calculated using modelling software/algorithms such as AGADIR (www.embl-heidelberg.de/Services/serrano/agadir/agadir-start.html) Muñoz & Serrano (1994) Nature Structural Biol 1, 399-409; Muñoz & Serrano (1994) J Mol Biol 245, 297-308; Muñoz & Serrano (1997) Biopolymers 41 495 509 and Lacroix et al (1998) J Mol Biol 284 173-191; PHD (Rost, B. et al, (1993) J Mol Biol 232, 584-599); PROF (Rost, B. et al, (1996) Methods Enzymol 266, 525-539); GOR4 (Garnier J et al (1978) J Mol Biol 120, 97-120; Garnier J et al (1996) Methods Enzymol 266, 540-553). Any suitable algorithms based on structural databases, structural preference databases or rotamer preference databases could be used for this calculation to estimate helical propensities, for example, GOR IV: J. Garnier. J. F. Gibrat and B. Robson in Methods Enzymol., vol 266, p 540-553 (1996). J. Garnier, D. Osguthorpe and B. Robson (J. Mol. Biol. 120,97, 1978). J Mol Biol 1987 Dec. 5; 198(3):425-443 (GOR-III); PHD: Rost B, Sander C. J Mol Biol 1993 Jul. 20; 232(2):584-99. Rost B, Sander C. Proteins 1994 May; 19(1):55-72; PREDATOR Frishman D, Argos P. Protein Eng 1996 February; 9(2):133-142; SIMPA/SIMPA96: Levin J M, Robson B, Garnier J. FEBS Lett 1986 Sep. 15; 205(2):303-308. J. LEVIN, J. GARNIER. Biochim. Biophys. Acta, (1988) 955, 283-295. Levin J M. Protein Eng. (1997),7, 771-776. SOPM/SOPMA Geourjon C, Deleage G. Protein Eng 1994 February; 7(2):157-164. Geourjon C, Deleage G. Comput Appl Biosci 1995 December; 11 (6):681-684.

Values of β-sheet propensity for all 20 amino acids can be determined using a published scale. A preferred scale is given in Table 1, which provides β-sheet propensity values for 19 amino acid residues (all except proline), these are normalised from 0 (high β-sheet propensity) to 1 (low β-sheet propensity). These data are from column 4 of Table 1 of Street and Mayo (1999) (Street, A. G. & Mayo, S. L. Intrinsic β-sheet propensities result from van der Waals interactions between side chains and the local backbone. *Proc. Natl. Acad. Sci. USA*, 96, 9074-9076 (1999)). The β-sheet propensity of proline is not reported due to the difficulty in determining it experimentally. The β-sheet propensity of glycine is obtained from theoretical calculations.

The invention further provides a computer system for determining aggregation rate data to predict an aggregation rate of a polypeptide with a defined amino acid sequence, the computer system comprising: a data store for storing data comprising hydrophobicity data, shape propensity data and charge data for a set of amino acids; a program store storing processor implementable code; and a processor, coupled to said program store and to said data store for implementing said stored code, the code comprising code for controlling the processor to: input an amino acid sequence for said polypeptide and data relating to at least one factor extrinsic to said amino acid sequence; determine a hydrophobicity value, a charge value, and at least one shape propensity value for said sequence; identify one or more aggregation-influencing patterns within said sequence; determine a pattern value for the sequence responsive to said identifying; and determine said aggregation rate data by determining a weighted combination of said hydrophobicity value, said charge value, said at least one shape propensity value, said pattern value and said extrinsic factor data.

The shape propensity value may comprise β-sheet propensity, for example expressed in terms of free energy, and may further comprise α-helix propensity, for example determined using code within the computer system or by means of a request sent to a separate computer system, for example over a network. A set of amino acids comprising, for example, all the natural amino acid residues may be employed.

The invention also provides computer program code to, when running, determine aggregation rate data to predict an aggregation rate of a polypeptide with a defined amino acid sequence, the code comprising code to: determine a hydrophobicity value, a charge value, and at least one shape propensity value for said sequence; identify one or more aggregation-influencing patterns within said sequence; determine a pattern value for the sequence responsive to said identifying; and determine said aggregation rate data by determining a weighted combination of said hydrophobicity value, said charge value, said at least one shape propensity value, said pattern value and at least one factor extrinsic to said amino acid sequence.

The program code may be provided on a data carrier or storage medium, such as a hard or floppy disk, ROM or CD-ROM, or on an optical or electrical signal carrier, for example as a disk image or DLL (dynamically linked library) via a communications network. Thus embodiments of the invention may be made available, or downloaded, or used via a web site. The processor control code may comprise program code in any conventional programming language for example C or assembler or machine code, and embodiments of the invention may be implemented on a general purpose computer system or in peptide synthesis apparatus, preferably apparatus for automatically synthesising a polypeptide based upon results obtained by applying the methods. The invention also encompasses polypeptides synthesised in this manner.

Figure 1:
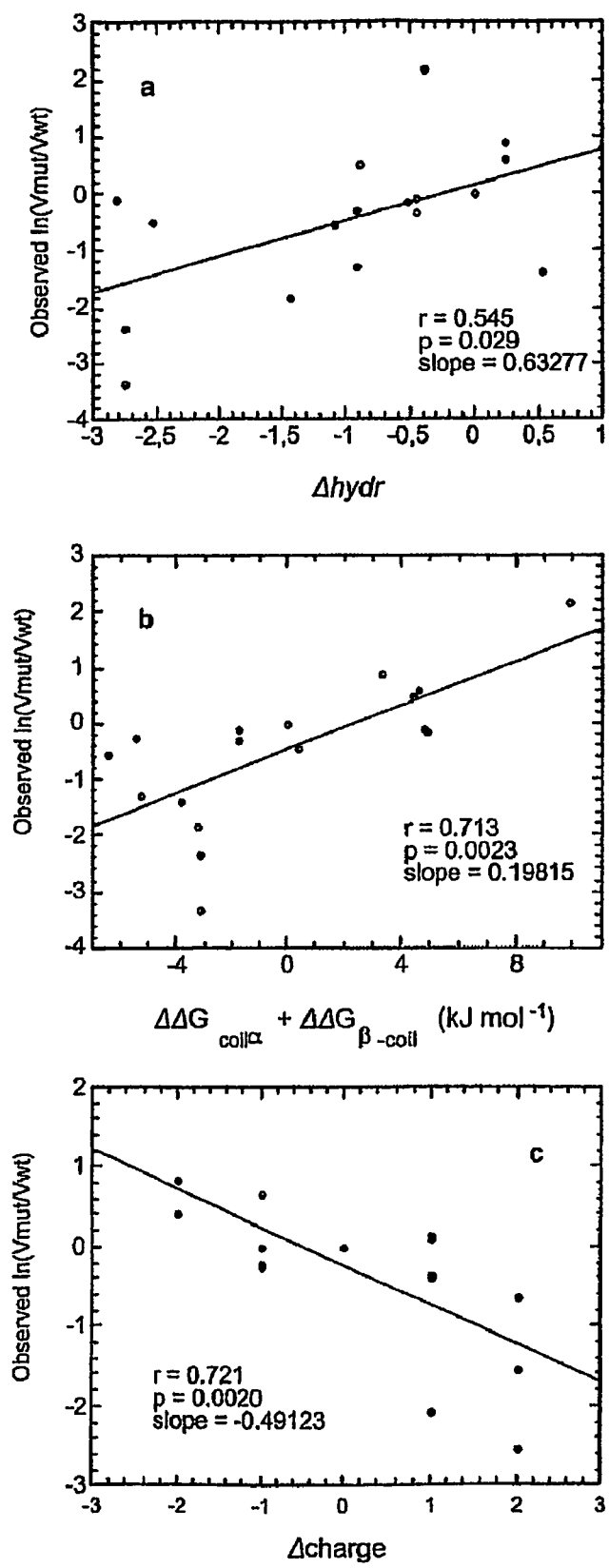
FIG. 1 shows the change of the aggregation rate of AcP resulting from mutation plotted against (a) the predicted change of hydrophobicity, (b) propensity to convert from an α-helical to a β-sheet conformation and (c) charge.

First we describe, as technical background helpful for understanding the invention, examples relating to the prediction of a relative aggregation rate of a polypeptide relative to a reference polypeptide. Then we describe, in Example 6, embodiments of the invention for "profiling" a polypeptide to identify sensitive regions for aggregation and, in Example 7, related embodiments of the invention for determining "absolute" polypeptide aggregation rates.

EXAMPLES

Example 1

AcP Experimental Work

The rates of aggregation for wild type AcP protein ($v_{wt}$) and for various AcP mutants (variants) ($v_{mut}$) were measured upon denaturation in 25% TFE, from time courses of ThT fluorescence, as described by Chiti et al., 2002a (Chiti, F., Taddei, N., Baroni, F., Capanni, C., Stefani, M., Ramponi, G. & Dobson, C. M. Kinetic partitioning of protein folding and aggregation. *Nature Struct. Biol.* 9, 137-143 (2002a)). All aggregation rate measurements were carried out under conditions in which all protein variants consist of ensembles of relatively unstructured conformations. The change of aggregation rate as a result of a mutation was expressed in all cases as the natural logarithm of the ratio of the aggregation rate constants of the mutant and wild-type protein ($\ln(v_{mut}/v_{wt})$).

In Table 1, the hydrophobicity values of the 20 amino acid residues at neutral pH are based on the partition coefficients from water to octanol. These data are from column 6 of Table 4.8 in Creighton (1993) (Creighton, T. E. In *Proteins. Structure and molecular properties. Second edition.* W. H. Freeman & Company (New York, 1993), p. 154.)). The β-sheet propensities of the 20 amino acid residues are normalised from 0 (high β-sheet propensity) to 1 (low β-sheet propensity). These data are from column 1 of Table 4 of Street and Mayo (1999) (Street, A. G. & Mayo, S. L. Intrinsic β-sheet propensities result from van der Waals interactions between side chains and the local backbone. *Proc. Natl. Acad. Sci. USA*, 96, 9074-9076 (1999)). The β-sheet propensity of proline is not reported due to the difficulty in determining it experimentally. The β-sheet propensity of glycine is obtained from theoretical calculations. The values of charge are at neutral pH. Values in brackets are at a pH lower than 6.0, when the histidine residue is positively charged.

TABLE 1

Scales of hydrophobicity, β-sheet propensity and charge for the 20 natural amino acids

| amino acid residue | hydrophobicity (kJ mol$^{-1}$) | β-sheet propensity | charge |
|---|---|---|---|
| Arg (R) | 3.95 | 0.35 | +1 |
| Lys (K) | 2.77 | 0.34 | +1 |
| Asp (D) | 3.81 | 0.72 | −1 |
| Glu (E) | 2.91 | 0.35 | −1 |
| Asn (N) | 1.91 | 0.40 | 0 |
| Gln (Q) | 1.30 | 0.34 | 0 |
| His (H) | 0.64 (2.87) | 0.37 | 0 (+1) |
| Ser (S) | 1.24 | 0.30 | 0 |
| Thr (T) | 1.00 | 0.06 | 0 |
| Tyr (Y) | −1.47 | 0.11 | 0 |
| Gly (G) | 0.00 | 0.60 | 0 |
| Pro (P) | −0.99 | n.d. | 0 |
| Cys (C) | −0.25 | 0.25 | 0 |
| Ala (A) | −0.39 | 0.47 | 0 |
| Trp (W) | −2.13 | 0.24 | 0 |
| Met (M) | −0.96 | 0.26 | 0 |
| Phe (F) | −2.27 | 0.13 | 0 |
| Val (V) | −1.30 | 0.13 | 0 |
| Ile (I) | −1.82 | 0.10 | 0 |
| Leu (L) | −1.82 | 0.32 | 0 |

Using the data in Table 1, the change of hydrophobicity (ΔHydr), propensity to convert from α-helical to β-sheet structure ($\Delta\Delta G_{coil-\alpha}+\Delta\Delta G_{\beta-coil}$) and change of charge (ΔCharge) were quantified for AcP using the tabulated values for all the amino acid residues.

The change in hydrophobicity (ΔHydr) resulting from mutation was calculated using $\Delta Hydr=Hydr_{wt}-Hydr_{mut}$, where $Hydr_{wt}$ and $Hydr_{mut}$ are the hydrophobicity values of the wild type and mutant residues, respectively (the values of hydrophobicity for all 20 amino acids are listed in Table 1).

To calculate the propensity to convert from α-helical to β-sheet structure ($\Delta\Delta G_{coil-\alpha}+\Delta\Delta G_{\beta-coil}$), it was necessary to calculate $\Delta\Delta G_{coil-\alpha}$ and $\Delta\Delta G_{\beta-coil}$.

The change of free energy for the transition random coil→β-sheet resulting from mutation ($\Delta\Delta G_{\beta-coil}$) was calculated using $\Delta\Delta G_{\beta-coil}=13.64\ (P_\beta^{wt}-P_\beta^{mut})$. $P_\beta^{wt}$ and $P_\beta^{mut}$ are the normalised β-sheet propensities of the wild-type and mutant residue, respectively (the values of β-sheet propensity for all 20 amino acids are listed in Table 1), and 13.64 is the conversion constant from the normalised scale to units of kJ mol$^{-1}$.

The predicted change of free energy for the transition α-helix→random coil resulting from mutation ($\Delta\Delta G_{coil-\alpha}$) was calculated using $\Delta\Delta G_{coil-\alpha}=RT\ \ln(P_\alpha^{wt}/P_\alpha^{mut})$. $P_\alpha^{wt}$ and $P_\alpha^{mut}$ are the predicted α-helical propensities (helix percentages) of the wild type and mutated sequences at the site of mutation, respectively which were calculated using the AGA-DIR algorithm at www.embl-heidelberg.de/Services/serrano/agadir/agadir-start.html); R=0.008314 kJ mol$^{-1}$ K$^{-1}$. (see also Lacroix, E., Viguera A R & Serrano, L. (1998). *J. Mol. Biol.* 284, 173-191).

The change of charge resulting from the mutation (ΔCharge) was calculated using ΔCharge=|Charge$_{mut}$|−|Charge$_{wt}$|, where |Charge$_{wt}$| and |Charge$_{mut}$| are the absolute values of charge for the wild-type and mutated sequences, respectively (obtained from the sums of the charge values of all residues reported in Table 1).

The change of aggregation rate upon mutation $\ln(v_{mut}/v_{wt})$ was plotted individually against ΔHydr, against ($\Delta\Delta G_{coil-\alpha}+\Delta\Delta G_{\beta-coil}$) and against ΔCharge, these plots are shown in FIGS. 1a, 1b and 1c, respectively.

The mutations reported in FIGS. 1a and 1b, described previously (Chiti et al., 2002a, ibid.), do not involve change of charge. The mutations reported in FIG. 1c, described previously (Chiti et al., 2002b, ibid.), were designed to minimise change of hydrophobicity and secondary structure propensities. Most of the amino acid substitutions of AcP involve residues within the two regions of the sequence, encompassing residues 16-31 and 87-98, that are thought to be relevant for aggregation.

The solid lines through the data represent the best fits to linear functions. The r and p values resulting from each correlation and the slope of the best fits are shown in each case.

In each of the analyses, the data points are considerably scattered around the lines representing the best fits to linear functions. This scatter can be attributed to the fact that only a single parameter is considered in each case, to the difficulty in predicting accurately changes in the hydrophobicity and secondary structure propensities, and to the varying relative importances of the different sites of mutation in the aggregation process. Despite the scatter present in each plot, however, the change of aggregation rate upon mutation ($\ln(v_{mut}/v_{wt})$) for AcP was found to correlate significantly with each of these parameters individually (FIGS. 1a, 1b, and 1c). The Despite the scatter present in each plot, however, the change of aggregation rate upon mutation ($\ln(v_{mut}/v_{wt})$) for AcP was found to correlate significantly with each of these parameters individually (FIGS. 1a, 1b, and 1c). Average dependency of $\ln(v_{mut}/v_{wt})$ on each parameter was calculated (the slope of the line of best fit resulting from each analysis. The values were found to be:

| | |
|---|---|
| ΔHydr | 0.633 |
| $\Delta\Delta G_{coil-\alpha}+\Delta\Delta G_{\beta-coil}$ | 0.198 |
| ΔCharge | 0.491 |

Following this analysis, Equation 1 was devised and used to determine the change of aggregation rate upon mutation ($\ln(v_{mut}/v_{wt})$ value):

$$\ln(v_{mut}/v_{wt})=0.633*\Delta Hydr+0.198*(\Delta\Delta G_{coil-\alpha}+\Delta\Delta G_{\beta-coil})-0.491*\Delta Charge$$

where the numbers preceding the parameters of ΔHydr, ($\Delta\Delta G_{coil-\alpha}+\Delta\Delta G_{\beta-coil}$) and ΔCharge are values for x, y and z respectively that correspond to the slopes of the three plots reported in FIG. 1 (i.e. the dependencies of $\ln(v_{mut}/v_{wt})$ on the three parameters).

Example 2

Figure 2:
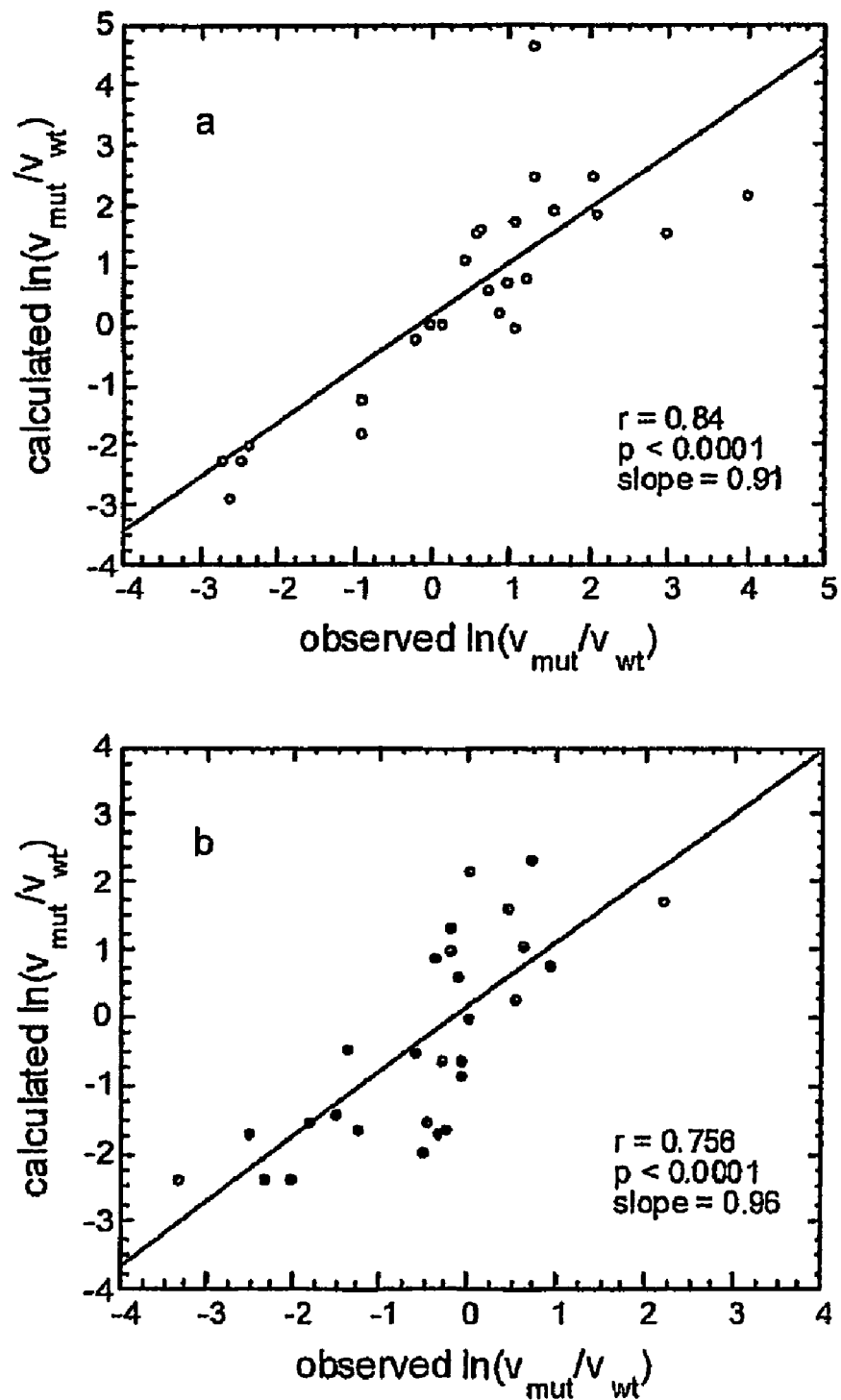
FIG. 2(a) shows the calculated versus observed change of the aggregation rate upon mutation for the short peptides or natively unfolded proteins listed in Table 2.
FIG. 2(b) shows the calculated versus observed change of the aggregation rate upon mutation for 27 amino acid substitutions of AcP within two regions of the sequence that appear to be relevant for aggregation and encompassing residues 16-31 and 87-98.

Comparison of Observed Versus Calculated Change in Aggregation Rate on Mutation of AcP Protein/Relative Aggregation Rates of Mutant AcP Proteins Using Equation 1, the change of aggregation rate $\ln(v_{mut}/v_{wt})$ was calculated for 27 amino acid substitutions of AcP within the two regions of the sequence that appear to be relevant for aggregation and encompassing residues 16-31 and 87-98. The change of aggregation rate for each mutation was determined experimentally, as described in Example 1, under conditions in which all protein variants consist of ensembles of relatively unstructured conformations. The calculated versus the experimental values of $\ln(v_{mut}/v_{wt})$ for all the mutations of AcP were plotted as shown in FIG. 2b. The observed correlation was found to be highly significant ($r=0.756$ and $p<0.0001$) and the slope was close to 1.

Example 3

Comparison of Observed Versus Calculated Change in Rate of Aggregation on Mutation for a Range of Polypeptides The combined function, Equation 1, was applied to calculate the change in aggregation rate upon mutation (calculated $\ln(v_{mut}/v_{wt})$) for 26 mutations in the polypeptides amylin, prion peptides, α-synuclein, amyloid β-peptide, tau, leucine rich repeat and a model peptide, as listed in Table 2.

Values for ΔHydr, $\Delta\Delta G_{coil-\alpha}+\Delta\Delta G_{\beta-coil}$ and ΔCharge were calculated for each polypeptide mutation using the methods described in Example 1.

The 26 mutations considered included both physiologically relevant mutations associated with genetic forms of protein deposition diseases and other substitutions that had been used in research to address specific issues. They were all mutations of either unstructured proteins (peptides), or polypeptides that appear to be natively unfolded, such as the amyloid β peptide, the islet amyloid polypeptide, α-synuclein, tau, short peptides dissected from the sequence of the prion protein and other model peptides. Only single-point mutations within short unstructured peptides or proteins that are unfolded under conditions close to physiological were considered in the analysis. All mutations were included for which actual experimental values of $\ln(v_{mut}/v_{wt})$ were directly available or could be determined from data in the literature. Mutations that acted simply by destabilising the native state of the protein involved were excluded. Data were considered regardless of the experimental techniques employed by the different authors to probe aggregation, provided a quantitative analysis could be carried out. When time or rate constants were not explicitly reported, the plots describing the kinetic profiles of aggregation were scanned and computer-analysed. This procedure allowed plots with numerical values of the data points to be reconstructed and analysed to obtain rate constant values. When lag and growth phases were evident in the kinetic profiles of aggregation, only the growth phase was considered. When data at fixed periods of time were reported (for example by means of bar graphs), the value for observed $\ln(v_{mut}/v_{wt})$ value was obtained from the ratio of the aggregation parameters of the mutated and wild-type protein (peptide), before equilibrium was reached.

Mutations involving proline residues were not analysed because of the difficulty in obtaining quantitative estimates of the change of β-sheet propensity as a result of these mutations (see Table 1). Nor were mutations considered when substantial discrepancies in the $\ln(v_{mut}/v_{wt})$ value were reported by different authors (when significant but not substantial discrepancies were present, we considered $\ln(v_{mut}/v_{wt})$ values resulting from averages of the available data).

TABLE 2

Changes of hydrophobicity, secondary structure propensities, charge and aggregation rate as a result of single-point mutations of unstructured peptides or natively unfolded proteins.

| Mutation | ΔHydr (kJ mol$^{-1}$) | $\Delta\Delta G_{\beta-coil}$ (kJ mol$^{-1}$) | $\Delta\Delta G_{coil-\alpha}$ (kJ mol$^{-1}$) | ΔCharge | calculated $\ln(v_{mut}/v_{wt})$ | observed $\ln(v_{mut}/v_{wt})$ | ref. |
|---|---|---|---|---|---|---|---|
| amylin | | | | | | | |
| N22A | 2.30 | −0.95 | −3.36 | 0 | 0.60 | 0.69 | 11 |
| F23A | −1.88 | −4.64 | −3.90 | 0 | −2.88 | −2.65 | 11 |
| G24A | 0.39 | 1.77 | −2.84 | 0 | 0.04 | −0.03 | 11 |
| I26A | −1.43 | −5.05 | −0.32 | 0 | −1.97 | −2.39 | 11 |
| L27A | −1.43 | −2.05 | 0.36 | 0 | −1.24 | −0.93 | 11 |
| S20G | 1.24 | −4.09 | 0.00 | 0 | −0.03 | 1.01 | 12 |
| prion peptides | | | | | | | |
| H111A | 3.26 | −1.36 | −3.21 | −1 | 1.65 | 0.60 | 13 |
| H111K | 0.10 | 0.41 | −1.72 | 0 | −0.20 | −0.26 | 13 |
| A117V | 0.91 | 4.63 | 2.37 | 0 | 1.96 | 1.51 | 13 |
| V210I | 0.52 | 0.41 | −0.97 | 0 | 0.22 | 0.84 | 14 |
| α-synuclein | | | | | | | |
| A53T | −1.39 | 5.59 | 2.83 | 0 | 0.79 | 1.18 | 15 |
| A76E | −3.30 | 1.64 | 0.00 | 1 | −2.25 | −2.72 | 16 |
| A76R | −4.34 | 1.64 | 0.64 | −1 | −1.80 | −0.93 | 16 |
| Amyloid-β peptide | | | | | | | |
| A21G | −0.39 | −1.77 | 3.27 | 0 | 0.05 | −0.07 | 17 |
| E22K | 0.14 | 0.14 | −1.72 | −2 | 0.76 | 0.92 | 18 |
| E22Q | 1.61 | 0.14 | 0.00 | −1 | 1.54 | 2.92 | 17, 18 |
| E22G | 2.91 | −3.41 | 4.30 | −1 | 2.51 | 2.03 | 19 |
| D23N | 1.90 | 4.36 | −1.72 | −1 | 2.22 | 3.97 | 17 |
| F19T | −3.27 | 0.95 | −1.76 | 0 | −2.23 | −2.48 | 20 |

TABLE 2-continued

Changes of hydrophobicity, secondary structure propensities, charge and aggregation rate as a result of single-point mutations of unstructured peptides or natively unfolded proteins.

| Mutation | ΔHydr (kJ mol$^{-1}$) | $\Delta\Delta G_{\beta\text{-coil}}$ (kJ mol$^{-1}$) | $\Delta\Delta G_{coil\text{-}\alpha}$ (kJ mol$^{-1}$) | ΔCharge | calculated ln($v_{mut}/v_{wt}$) | observed ln($v_{mut}/v_{wt}$) | ref. |
|---|---|---|---|---|---|---|---|
| Tau | | | | | | | |
| G272V | 1.30 | 6.41 | −1.71 | 0 | 1.75 | 1.04 | 21, 22 |
| R406W | 6.08 | 1.50 | 0.00 | −1 | 4.64 | 1.25 | 21, 22, 23 |
| Y310W | 0.66 | −1.77 | 0.00 | 0 | 0.07 | 0.05 | 23 bis |
| Leucine-rich repeat | | | | | | | |
| D24N | 1.90 | 4.36 | −3.43 | −1 | 1.88 | 2.08 | 24 |
| D24Q | 2.51 | 5.18 | −3.10 | −1 | 2.49 | 1.25 | 24 |
| Model peptide | | | | | | | |
| D6E | 0.90 | 5.04 | −2.27 | 0 | 1.12 | 0.40 | 25 |
| D6N | 1.90 | 4.36 | 0.00 | 1 | 1.57 | 0.52 | 25 |

Here we describe the way we utilised the experimental data from the literature to determine the experimental values of ln($v_{mut}/v_{wt}$) for each of the mutations reported in Table 2 above: mutations of amylin: Experimental data of ln($v_{mut}/v_{wt}$) were all calculated from FIG. 2B (data points at 4 min) of ref. 13; S20G mutation of amylin: Experimental data of ln($v_{mut}/v_{wt}$) on the S20G mutation of amylin were from FIG. 5 of ref. 14. Data were replotted to obtain rate constants within the elongation phases. The value of ln($v_{mut}/v_{wt}$) considered in our analysis is the average of the two ln($v_{mut}/v_{wt}$) values obtained from the two reported concentrations; H111A, H111K and A117V mutations of a prion peptide: Experimental data of ln($v_{mut}/v_{wt}$) on the 106-126 peptide of the human prion were from FIG. 2 of ref. 15. Data were replotted to determine the initial rates of monomer depletion; V210I mutation of a prion peptide: Experimental data of ln($v_{mut}/v_{wt}$) on the 198-218 peptide of the human prion were from FIG. 8 (aggregation rates were taken from the slopes of the reported plot) of ref. 16; A53T mutation of α-synuclein: Experimental data of ln($v_{mut}/v_{wt}$) on the A53T mutation of α-synuclein were from ref. 17: data were taken from FIG. 1B (time of 14 days), FIG. 2A (time of 49 days) and from FIG. 3A (time 66 days). The reported value of ln($v_{mut}/v_{wt}$) results from an average of the three values; A76E and A76R mutations of α-synuclein: Experimental data of ln($v_{mut}/v_{wt}$) on the A76E and A76R mutations of α-synuclein were from FIG. 3 (time of 2 days) of ref. 12; A21G and D23N mutations of Aβ: Experimental data of ln($v_{mut}/v_{wt}$) on the A21 G and D23N mutations of Aβ were from FIG. 3 of ref. 18: data were replotted to obtain the rate of depletion of Congo red. This implied considering the rate of the first 6 hr for the D23N mutant (before the equilibrium was reached) and between 0 and 48 hr for the A21G and wild-type peptides; E22K mutation of Aβ: Experimental data of ln($v_{mut}/v_{wt}$) on the E22K mutation of Aβ were from FIG. 2 of ref. 19: the data points were replotted and fitted to a single exponential function to obtain rate constant values; E22Q mutation of Aβ: Experimental data of ln($v_{mut}/v_{wt}$) on the E22Q mutation of Aβ were from (1) FIG. 2 of ref. 19: the data points were replotted and fitted to a single exponential function to obtain rate constant values; (2) FIG. 3 of ref. 18: data were replotted to obtain the rate of depletion of Congo red; this implied considering the rate of the first 6 hr for the E22Q mutant (before the equilibrium was reached) and between 0 and 48 hr for the wild-type peptide. The reported value of ln($v_{mut}/v_{wt}$) results from an average of the two values; E22G mutation of Aβ: Experimental data of ln ($v_{mut}/v_{wt}$) on the E22G mutation of Aβ were from FIG. 5a,b of ref. 20: data were replotted to obtain the rate of depletion of monomer/dimer. This implied considering the rate of the first 5 hr for the E22G mutant (before the equilibrium was reached) and between 0 and 50 hr for the wild-type peptide; F19T mutation of Aβ: Experimental data of ln($v_{mut}/v_{wt}$) on the F19T mutation of Aβ were from FIG. 4 of ref. 21: similar values of ln($v_{mut}/v_{wt}$) are obtained at different Aβ concentrations; R5L mutation of tau: Experimental data of ln ($v_{mut}/v_{wt}$) on the R5L mutation of tau were from FIG. 5 of ref. 22: the data points were replotted and fitted to a single exponential function (for the wild-type protein) or a double exponential function (for the mutant) to obtain rate constant values; experimental data of ln($v_{mut}/v_{wt}$) were calculated for both phases observed for the mutant. The reported value of ln($v_{mut}/v_{wt}$) results from an average of the two values; G272V mutation of tau: Experimental data of ln($v_{mut}/v_{wt}$) on the G272V mutation of tau were from (1) Table 1 (time constants) of ref. 24; (2) FIGS. 5 and 6 (rates during elongation phases) of ref. 23. The reported value of ln($v_{mut}/v_{wt}$) results from an average of the three values; R406W mutation of tau: Experimental data of ln($v_{mut}/v_{wt}$) on the R406W mutation of tau were from Table 1 (time constants) of ref. 24, FIG. 5 (rates during elongation phases) of ref. 23 and from FIG. 1 (rates during elongation phases) of ref. 25. The reported value of ln ($v_{mut}/v_{wt}$) results from an average of the three values; Y310W mutation of tau: Experimental data of ln($v_{mut}/v_{wt}$) on the Y310W mutation of tau were from FIG. 3A of ref. 26: the data points in the presence of heparin were replotted and fitted to single exponential functions to obtain rate constant values; Mutations of the leucine rich repeat peptide: Experimental data of ln($v_{mut}/v_{wt}$) on the leucine-rich repeat were from FIG. 2 ref. 27. The aggregation rates were taken from the slopes of the reported plot; mutations of the VTVKVDAVKVTV (SEQ ID NO:1) peptide: Experimental data of ln($v_{mut}/v_{wt}$) on the 12 residue model peptide were from FIG. 8 of ref. 28 (mean residue ellipticity at the peak in the 215-220 nm region subtracted by mean residue ellipticity for random coil obtained from FIG. 6a).

The calculated versus the experimental value of $\ln(v_{mut}/v_{wt})$ was plotted and is shown in FIG. 2(a). The highly significant correlation (r=0.84, p<0.0001), and the value of the slope that is close to 1.0, indicate close agreement between calculated and experimental effects of mutations on the aggregation rates of this heterogeneous group of polypeptides. The observed changes of aggregation rate upon mutation span a range of ca. 800 times, i.e. from 15 slower to 53 faster than the corresponding wild-type polypeptide (FIG. 2a and Table 2). 84% of these mutations have calculated values of $\ln(v_{mut}/v_{wt})$ that vary within a factor of 3 from the observed values of $\ln(v_{mut}/v_{wt})$. The percentage rises to 92% and 96% if spread factors of 5 and 10 are considered, respectively. Examples where close agreement is found between theoretical and experimental values include mutations associated with hereditary spongiform encephalopathies, such as the A117V and V210I substitutions of the prion protein (Table 2). Predicted and experimental values are in close agreement also for the A53T mutation associated with early-onset Parkinson's disease and for various mutations associated with the amyloid β-peptide and responsible for either early-onset Alzheimer's disease or hereditary cerebral haemorrhage with amyloidosis (Table 2).

If the analysis is repeated using only one single determinant to calculate the $\ln(v_{mut}/v_{wt})$ values, significant correlations were still found between calculated and observed values of $\ln(v_{mut}/v_{wt})$ (p=0.0003 using only ΔHydr to calculate $\ln(v_{mut}/v_{wt})$, p=0.036 using only $\Delta\Delta G_{coil-\alpha}+\Delta\Delta G_{\beta-coil}$ and p=0.011 using only ΔCharge). Nevertheless, these correlations are less remarkable than that observed when considering a combination of all three factors and the slopes are significantly less than 1.0 (0.61, 0.19 and 0.10 using only ΔHydr, only $\Delta\Delta G_{coil-\alpha}+\Delta\Delta G_{\beta-coil}$ and only ΔCharge, respectively). This demonstrates that the equation in which these factors are combined gives a more accurate method for determining the ratio of rate of aggregation for modified (e.g. mutant) and reference (e.g. wild type) polypeptides.

The correlation shown in FIG. 2(a) between theoretical and experimental effects of mutations on aggregation was found to be striking, considering the heterogeneous group of protein and peptide systems used in the analysis as well as the variability of sites at which the various mutations occur.

Example 4

Applicability of the Algorithm to Modifications Involving Several Amino Acid Residues and the Use of Kinetic Parameters other than "Aggregation Rates"

Equation 1 was tested against other systems to evaluate its applicability to broader systems. Calculations used to derive Equation 1 are based on the aggregation kinetics experienced by protein and peptide variants that differ in a single residue from the original sequence. The rates ($v_{mut}$ and $v_{wt}$) used in the expression correspond to the exponential phase of aggregation for each one of the peptides, and do not include any possible lag period or nucleation phase preceding that stage.

To test the validity of this expression in predicting the aggregation propensities of peptides derived from two Calcitonin variations were included. The first was to evaluate if the effect of several substitutions could be predicted in the same manner the algorithm was able to do with single point mutations. The second was to include as a kinetic parameter the relative ratio of aggregation times ($\tau_{mut}/\tau_{wt}$). By including the effect of a lag phase on the kinetics of aggregation exhibited by the peptides, the aggregation times for each one of the peptides (τ), could be defined in two different ways: the first one was the nucleation time or time that precedes the initiation of aggregation or the development of turbidity in the solution (T1), and the second one would correspond to the half time of aggregation or the time at which variations in the measurements used for monitoring aggregation (light scattering, or any other method) reached half of it maximum value (T2). This might enable the application of the equation to the prediction of aggregation propensities for a much broader range of molecules with important design aspects.

The calculations were made on two variants of Calcitonin, using data available in the literature (Arvinte, et al. 1993, J Biol Chem 268: 6415-6422), and previous studies included in another patent application by some of the members of the group (Zurdo & Dobson, WO 02/083734, PCT/GB02/01778). The calculations were made using data disclosed in those publications, producing the values indicated in table 3. In both cases the value for the $\tau_{wt}$ parameter was obtained independently.

TABLE 3

Predicted and experimental changes in times of aggregation exhibited by various calcitonin peptides when compared to the human sequence.

| | Calculated $\ln(v_{mut}/v_{wt})$ | Observed $\ln(v_{mut}/v_{wt})$ | Calculated $(\tau_{mut}/\tau_{wt})$ | Observed $(\tau_{mut}/\tau_{wt})$ |
|---|---|---|---|---|
| [1]Salmon-1 | −10.54 | −10.31 | 37,681.05 | ~30,000[a] |
| [2]SEQ ID NO 14 | −5.60 | −4.61[b]/−5.71[a] | 271.70 | 100[b]/300[a] |

[1]Data obtained from Arvinte et al. (1993) J Biol Chem 268, 6415-6422. Salmon calcitonin has 16 modified positions when compared to the human sequence.
[2]Sequence reported in Zurdo & Dobson (WO 02/083734, PCT/GB02/01778), and Zurdo & Dobson (unpublished observations). Sequence ID NO 14 show 6 modified positions when compared to the human sequence.
[a]Values for calculating τ were obtained using T1 as described above.
[b]Values for calculating τ were obtained using T2 as described above.

Calculations for changes in aggregation time were made assuming the following relations with aggregation rates described by equation 1.

$$(\tau_{mut}/\tau_{wt})=(v_{wt}/v_{mut})=1/\exp(\ln(v_{mut}/v_{wt}))$$

This analysis shows that equation 1 can be used to predict the aggregation behaviour of a given polypeptide that has more than one amino acid modification compared to the original polypeptide sequence. Moreover, it suggests that in systems where a lag phase is present, or the aggregation rate can be difficult to calculate, alternative kinetic parameters represented by the times of aggregation (either T1—nucleation time—or T2—half time of aggregation—) can provide valid values to compare with the predictions given by Equation 1.

Example 5

Applicability of the Algorithm to Modifications Involving Addition or Deletion of Amino Acid Residues: Aβ Peptides Linked with Alzheimer's Disease Peptides Aβ(1-40) and Aβ(1-42) that are associated with Alzheimer's disease show differences in their aggregation propensities. The peptides differ in sequence only by two residues at the C-terminus. The methods of the invention explain the higher propensity to aggregate of the 42 residues form, relative to the 40 residues form, of the amyloid β peptide associated with Alzheimer's disease (Jarrett et al., 1993). Indeed, although the α-helical propensity and charge of the entire peptide appear to be unchanged upon addition of the dipeptide Ile-Ala at the C-terminus, the values of hydrophobicity and β-sheet propensity of the two residues are higher than the average values calculated over the entire peptide.

From a quantitative point of view, the change of hydrophobicity resulting from the addition of the two residues at the C-terminus can be calculated as $\Delta Hydr = Hydr_{wt} - Hydr_{mut}$, where $Hydr_{mut}$ is the average hydrophobicity of the 40 residues forming the short form of the peptide; $Hydr_{mut}$ is the average hydrophobicity of the two inserted residues (Ile-Ala). The change of β-sheet propensity resulting from insertion can be calculated similarly. This leads to the prediction that the long form aggregates 7 times faster than the short form, in good agreement with the kinetic profile reported by Jarrett et al., 1993 who found acceleration of 7-8 times (Jarrett J T, Berger E P, Lansbury P T Jr. The carboxy terminus of the beta amyloid protein is critical for the seeding of amyloid formation: implications for the pathogenesis of Alzheimer's disease. *Biochemistry*, 32, 4693-4697 (1993)).

Aggregation Rates—Example

An aggregation rate may be defined by a rate constant in an aggregation equation, for example aggregation=$A(1-e^{-kt})$ where t is time. Aggregation may be measured, for example, in terms of a time period for, say, 50% aggregation. In the equations described herein either an aggregation rate or a log (preferably natural log) aggregation rate may be employed.

In practice a degree of aggregation or aggregation rate constant may be determined by, for example, turbidity or light scattering, or one of many other means—for example from kinetic traces obtained by the following methods: ThT fluorescence, turbidity, CD, or direct mass/volume analyses, such as sedimentation, size exclusion chromatography, and filtration. However although these methods detect slightly different aspects of aggregation they are closely linked, and the (log) aggregation rate measured is approximately independent of the measuring technique employed.

In some cases aggregation is a 'spontaneous' event preceded by a time lag and in these cases the aggregation rate may correspond to the time lag prior to the onset of aggregation. Such a measure of aggregation rate appears to be related to the aforementioned aggregation rate constant but may not directly correspond. In some cases seeded and non-seeded systems result in nearly identical aggregation rates if the lag phase in the non-seeded system is disregarded, but this is not always the case. The equations described herein, depending upon the scaling factors, may be employed for either or both of these types of aggregation rate measurement.

Due to difficulties in quantifying 'stirring' and its influence on kinetics this was not considered in the examples described herein, although the effects of stirring could be included in the equations described herein.

Example Computer System Implementing the Above-Described Methods

Figure 3:
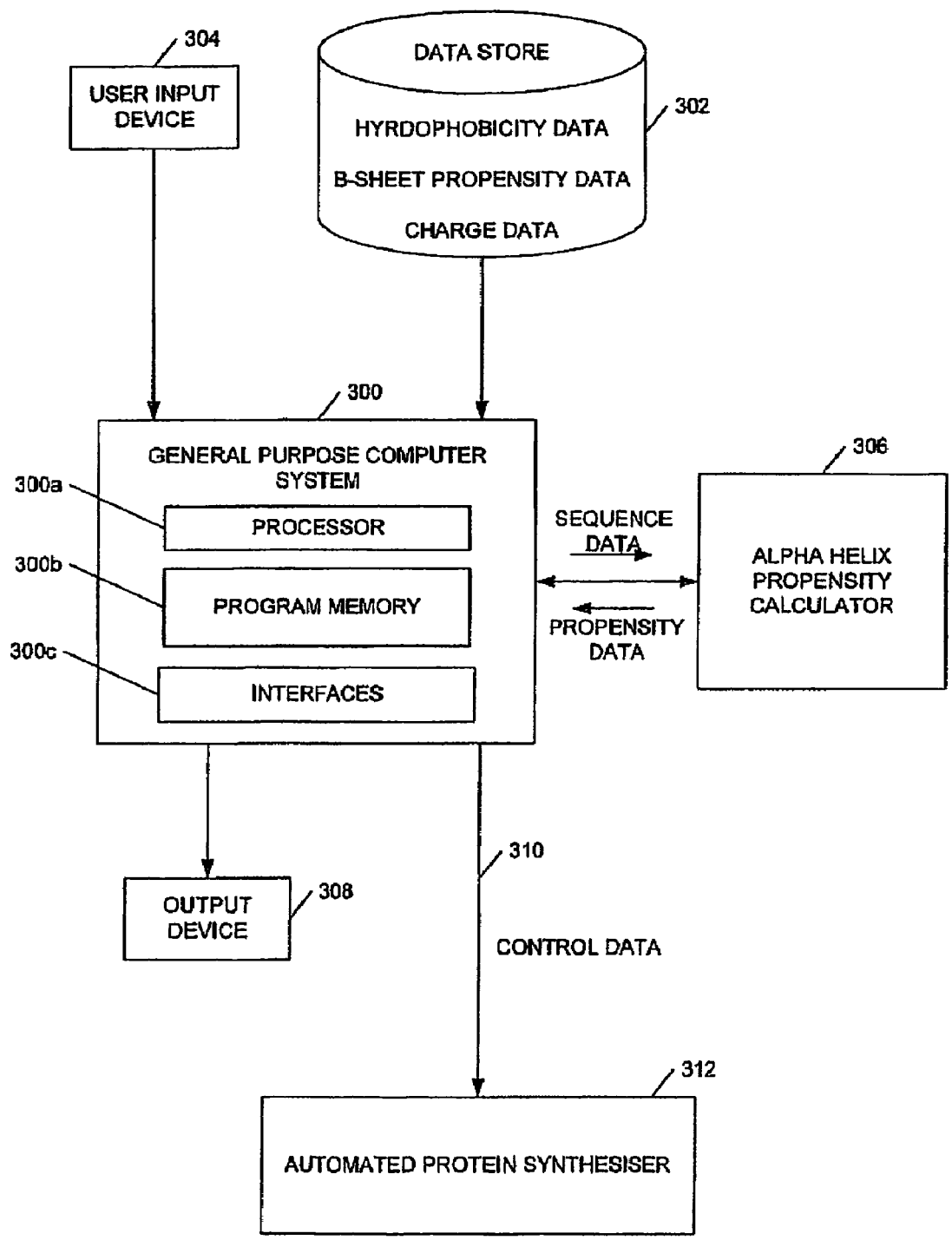
FIG. 3 shows a block diagram of a computer system for implementing a first aggregation rate determination procedure.

Referring now to FIG. 3, this shows a block diagram of a computer system for implementing the above-described method. A general purpose computer system 300 comprises a processor 300a coupled to programme memory 300b storing computer programme code to implement the method, as described further below, and interfaces 300c such as conventional computer screen, keyboard, mouse, and printer, as well as other interfaces such as a network interface, a control interface for a peptide synthesiser and software interfaces such as a database interface. The computer system 300 accepts user input from an input device 304 such as a keyboard, input data file, or network interface, and provides an output to an output device 308 such as a printer, network interface, or data storage device. Input device 304 receives an input comprising an amino acid sequence for the modified (e.g. mutant) peptide as well as pH and temperature values appropriate to an environment for which the aggregation rate of the polypeptide is determined. A glycine/proline correction factor, such as a weight for a structural distortion factor interfering with inter-molecular β-sheet formation or aggregation, may also be inputted. The output device 308 provides a comparative aggregation rate information such as a log (base 10 or natural) aggregation ratio, for example, a ratio of half times for aggregation of a mutant as compared with a wild type polypeptide.

Computer system 300 is coupled to a data store 302 which stores hydrophobicity data, β-sheet propensity data (either as propensity data per se or in terms of free energy) and charge data. This data is stored for each amino acid (residue) and preferably a plurality of sets of each of these data types is stored corresponding to different values of pH and temperature. The computer system, in the illustrated example, is shown interfacing with an α-helix propensity calculator 306. This may be a separate machine, for example, coupled to computer system 300 over a network, or may comprise a separate programme running on general purpose computer system 300, or in other examples α-helix propensity code may be stored within programme memory 300b and operate in a unitary fashion with the aggregation rate determination code described below. However whichever method is employed the α-helix propensity calculator receives sequence data, indirectly from the user input device, and provides α-helix propensity data in return. This data and the data in data store 302 may either be determined on an amino acid by amino acid basis or may be determined taking into account sequence context, for example, using a window over the sequence to modify data values dependent upon neighbouring amino acids.

As illustrated, computer system 300 may also provide a data control output 310 to an automated peptide synthesiser 312. The control data will generally comprise an amino acid sequence of a polypeptide. In this way computer system 300 may be programmed to automatically compare the properties of a number of modified (e.g. mutant) polypeptides and select one or more of those which are predicted to have favourable properties for automated synthesis. An example of such an automated peptide synthesiser would be an ABI 433A Peptide Synthesiser (Applied Biosystems).

Figure 4:
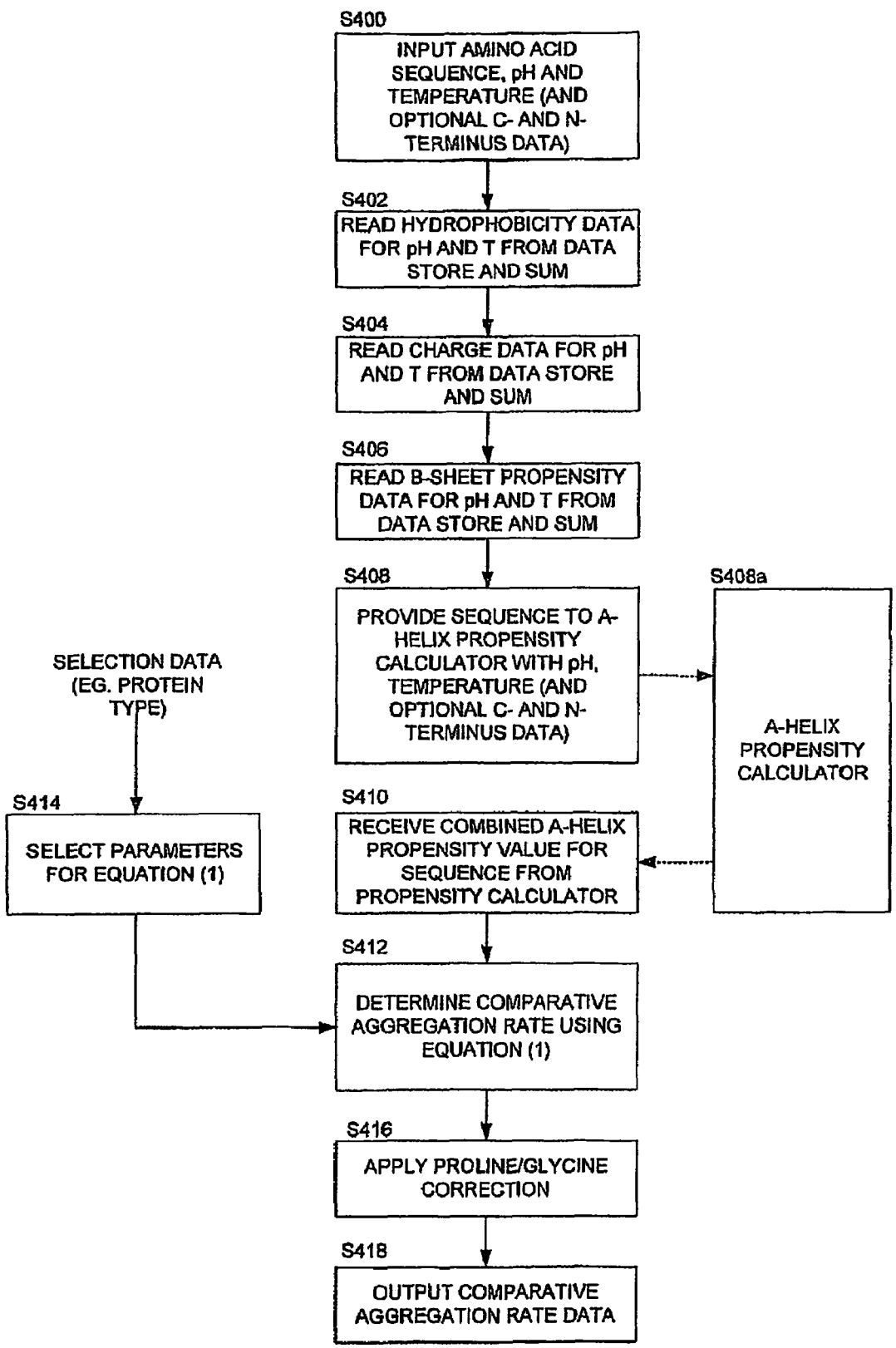
FIG. 4 shows a flow diagram of a comparative aggregation rate determination procedure.

Referring next to FIG. 4, this shows a procedure for determining a comparative aggregation rate along the lines described above. FIG. 4 represents a flow diagram of an example of code running in programme memory 300b of FIG. 3.

At step S400 a user inputs an amino acid sequence, pH and temperature data, optionally with C- and N-terminus data for the sequence. Then at step S402 the computer system reads hydrophobicity data for the input sequence from the data store and sums this to provide an estimate of hydrophobicity for the peptide coded by the sequence. Where, as is strongly preferable, data for a range of pH and temperature values is available, data most closely corresponding to the desired pH and temperature is retrieved. Then as steps S404 and S406, the procedure reads charge data and β-sheet propensity data from the data store in a similar manner, summing the charge data to provide a charge estimate for the polypeptide corresponding to the input sequence and, similarly, summing the β-sheet propensity data (normally expressed in terms of free energy). With proline, no β-sheet propensity value is available and so a proline residue may be skipped when summarising these values or an arbitrary β-sheet propensity value or one corresponding to another amino acid may be employed. For example, if β-sheet propensity is expressed in terms of free energy, an arbitrary value of 1, or a value corresponding to another amino acid can be used. Optionally steps S402 and S406 may employ a "window" (for example of 3, 5, 7, or more amino acids) that would include a correction for the effect of flanking residues on the properties of a particular amino acid, (i.e. to take account of near neighbours within an amino acid sequence), rather than considering each amino acid of the sequence individually.

Step S408 the procedure provides the input sequence to an α-helix propensity calculator, with the pH and temperature data, and, where available, with the C- and N-terminus data. An α-helix propensity calculator S408a operates on this data and returns data back to the procedure at step S410, the returned data comprising an α-helix propensity value for the complete sequence. Suitable programme code for α-helix propensity calculator S408a comprises the AGADIR code available from http://www.embl-heidelberg.de/Services/serrano/agadir/agadir-start.html, GOR4 code available from http://npsa-pbil.ibcp.fr/cgi-bin/npsa_automat.pl?page=npsa_gor4.html and other codes described above. The skilled person will recognise that, if desired, this code or a newly designed code derived from publicly accessible (described in the scientific literature) or additional experimental data may be incorporated within the code implementing the procedure of FIG. 4 rather than being implemented as a separate procedure.

At step S412 the procedure then determines the comparative aggregation rate of the polypeptide defined by the input amino acid sequence as compared with a reference polypeptide, using equation 1 above. It can be seen from equation 1 that a determination of comparative aggregation rate requires a difference in hydrophobicity, secondary structural propensity, and charge, and values for hydrophobicity, secondary structural propensity and charge for the reference polypeptides may either be determined by repeating steps S400 to S410 for the reference polypeptide or by reading stored values of these parameters from data store 302, or in any other conventional manner. If desired at step S412 the parameters or scaling factors in equation 1 operating on the differences in hydrophobicity, structural propensity and charge can be selected from sets of suitable parameters (step S414) in response to input data such as polypeptide type data. For example, a completely random coil polypeptide may use different parameters to a partially unfolded or structured polypeptide. Also, a polypeptide rich in a specific type of residue, such as aromatic or charged amino acids, may require different parameters.

After determining the comparative aggregation rate an optional correction may be applied at step S416 for proline and or glycine residues in order to account for additional conformational or structural preferences that may hinder formation of inter-molecular β-sheet or aggregated structures by a given polypeptide and then at step S418 the system outputs the result of the comparative aggregation rate calculation. This may comprise a simple positive or negative value indicating whether the aggregation rate of the modified polypeptide (e.g. mutant) is greater or less than that of the reference polypeptide, but preferably this comprises quantitative data relating to the comparative aggregation rates such as a log aggregation rate ratio.

Figure 5:
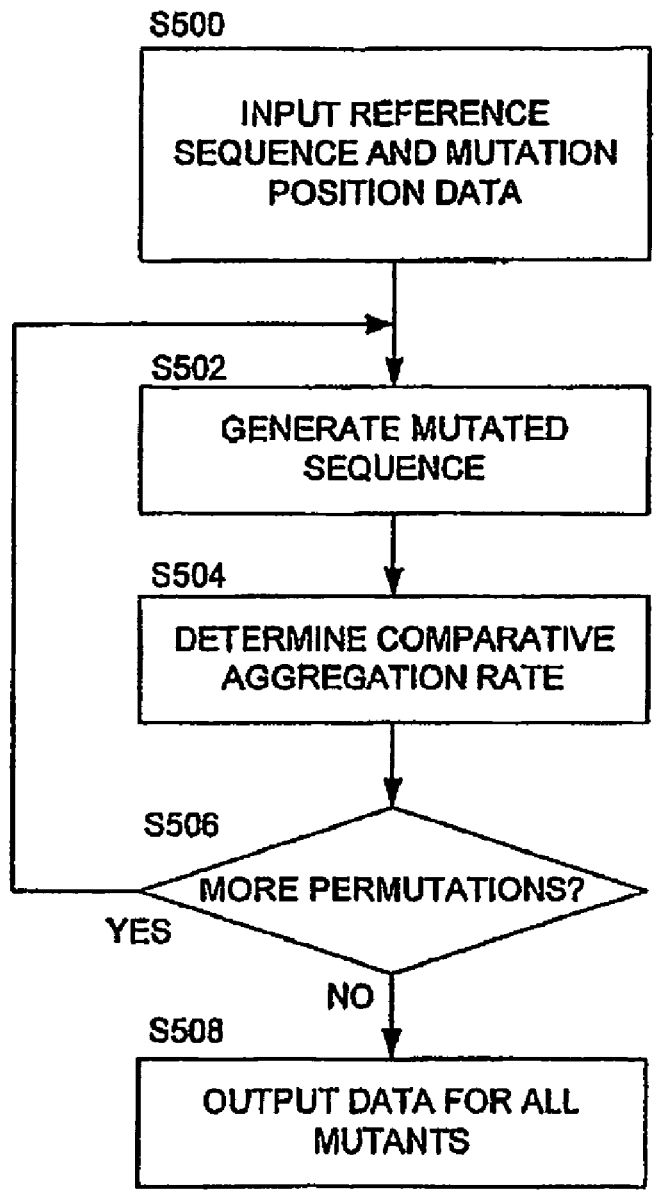
FIG. 5 shows a flow diagram of an automated protein synthesis candidate determination procedure.

FIG. 5 shows a flow diagram of one advantageous implementation of the procedure of FIG. 4. In particular FIG. 5 shows a method of screening modified polypeptides (e.g. mutations) in order to select candidates with promising properties for further investigation and, optionally, synthesis. Thus at step S500 an amino acid sequence for a reference polypeptide is input together with data identifying one or more modified (e.g. mutant) positions. Optionally the procedure may also allow a modification or range of modifications to be specified, for example in terms of a pre-determined set or selection of amino acids.

Following initialisation, at step S502 the procedure generates a modified sequence representing one of the possible permutations defined by the input data and then, at step S504, determines a comparative aggregation rate for modified polypeptide in comparison with the reference polypeptide, for example using the procedure at FIG. 4. Then, at step S506, the procedure checks whether there are any more permutations for which to perform the calculation, and if so returns to step S502 until a complete set of possible permutations has been generated. Then, at step S508, the set of comparative aggregation rate data for each modified polypeptide (in comparison with the reference protein) is output, for example as an autolist, graph, or in any other convenient manner. This data may then be used, for example to identify candidates for synthesis and/or for comparison with other data such as immunogenicity/antigenicity. In particular, one or more of the 'best' modified polypeptides, for example mutants with a particularly high or low aggregation rate, may be collected and the sequence data for these modified polypeptides output to an automated peptide synthesiser such as synthesiser 312 of FIG. 3 to automatically produce the mutant proteins for, say, further investigation.

Example 6

Intrinsic Propensities for Amyloid Formation of Amino Acids and Polypeptide Sequences: Identification of the Sensitive Regions for Aggregation We now present a formula to measure the intrinsic amyloid aggregation propensity of a polypeptide. From this formula, we identify the residues that promote amyloid formation, compare the amyloid propensities of a number of sequences, and identify the regions of the sequence that are particularly important to promote aggregation.

Defining Aggregation Propensities

The intrinsic factors of the algorithm described above were used to define a new equation specifying $P_{agg}$ as the intrinsic aggregation propensity of a sequence. The weight for each intrinsic and extrinsic factor was simultaneously determined using regression techniques on a dataset of 83 sequences, as set out in Table 4 below. The weights for the intrinsic factors were taken from the resulting algorithm and used to define a further $P_{agg}$ equation (Equation 2).

TABLE 4

| sequence | mutants | pH | ionic strength | [peptide] | references |
| --- | --- | --- | --- | --- | --- |
| AcP | 59 | 5.5 | 43 mM | 0.04 mM | [3, 4, 77] |
| Aβ40 | 2 | 7.4 | 150 mM | 0.25 mM | [66] |
| Aβ40 | none | 7.4 | 81 mM | 0.03 mM | [80] |
| Aβ42 | none | 7.4 | 81 mM | 0.01 mM | [80] |
| ABri | none | 9.0 | 89 mM | 1.31 mM | [102] |
| AChE peptide 586-599 | none | 7.0 | 7.7 mM | 0.20 mM | [109] |
| Amylin 1-37 | 2 | 7.2 | 1.1 mM | 2.0 mM | [67] |

TABLE 4-continued

| sequence | mutants | pH | ionic strength | [peptide] | references |
|---|---|---|---|---|---|
| Amylin 1-37 | none | 7.3 | 1.4 mM | 0.14 mM | [89] |
| Amylin 8-37 | none | 7.3 | 1.4 mM | 0.14 mM | [89] |
| IAPP precursor | none | 5.0 | 0.1 mM | 0.001 mM | [88] |
| LRR | 1 | 7.8 | 3.3 mM | 0.39 mM | [64] |
| PrP peptide 106-126 | 3 | 5.0 | 1.2 mM | 0.33 mM | [65] |
| TTR | 3 | 4.4 | 130 mM | 0.014 mM | [68] |

The references are as follows:
[3]: Chiti, F., et al., Kinetic partitioning of protein folding and aggregation. Nat Struct Biol, 2002a. 9(2): p. 137-43;
[4]: Chiti, F., et al., Studies of the aggregation of mutant proteins in vitro provide insights into the genetics of amyloid diseases. Proc Natl Acad Sci USA, 2002b. 99 Suppl 4: p. 16419-26;
[64]: Symmons, M. F., et al., X-ray diffraction and far-UV CD studies of filaments formed by a leucine-rich repeat peptide: structural similarity to the amyloid fibrils of prions and Alzheimer's disease beta-protein. FEBS Lett, 1997. 412(2): p. 397-403;
[65]: Salmona, M., et al., Molecular determinants of the physicochemical properties of a critical prion protein region comprising residues 106-126. Biochem J, 1999 342 (Pt 1): p. 207-14;
[66]: Miravalle, L., et al., Substitutions at codon 22 of Alzheimer's abeta peptide induce diverse conformational changes and apoptotic effects in human cerebral endothelial cells. J Biol Chem, 2000. 275(35): p. 27110-6;
[67]: Azriel, R. and E. Gazit, Analysis of the minimal amyloid-forming fragment of the islet amyloid polypeptide. An experimental support for the key role of the phenylalanine residue in amyloid formation. J Biol Chem, 2001, 276(36): p. 34156-61;
[68]: Hammarstrom, P., et al., Sequence-dependent denaturation energetics: A major determinant in amyloid disease diversity. Proc Natl Acad Sci USA, 2002. 99 Suppl 4: p. 16427-32;
[80]: Fezoui, Y. and D. B. Teplow, Kinetic studies of amyloid beta-protein fibril assembly. Differential effects of alpha-helix stabilization. J Biol Chem, 2002, 277(40): p. 36948-54;
[88]: Kayed, R., et al., Conformational transitions of islet amyloid polypeptide (IAPP) in amyloid formation in vitro. J Mol Biol, 1999. 287(4): p. 781-96;
[89]: Goldsbury, C., et al., Amyloid fibril formation from full-length and fragments of amylin. J Struct Biol, 2000. 130(2-3): p. 352-62;
[102]: El-Agnaf, O. M., et al., Effect of the disulfide bridge and the C-terminal extension on the oligomerization of the amyloid peptide ABri implicated in familial British dementia. Biochemistry, 2001. 40(12): p. 3449-57;
[109]: Cottingham, M. G., M. S. Hollinshead, and D. J. Vaux, Amyloid fibril formation bya synthetic peptide from a region of human acetylcholinesterase that is homologous to the Alzheimer's amyloid-beta peptide. Biochemistry, 2002. 41(46): p. 13539-47.

Predicting Aggregation Propensities

The aggregation propensities of a number of peptides and small proteins were calculated at neutral pH. Those included were Alzheimer's α-peptides (Ab40& Ab42), ABri, acetylcholinesterace peptide (586-599) (AchE peptide), acylphosphatase (AcP), amylin peptide (1-37), the SH3 domain of α-spectrin, the SH3 domain of phosphatidylinositol 3-kinase (PI3 SH3), α-synuclein, β2 microglobulin (β2m), calcitonin, the N-terminal domain of prokaryotic protein HypF (HypF), insulin, leucine rich repeats (LRR), prion protein (PrP), PrP peptide (106-126), and transthyretin (TTR).

Amino Acid Aggregation Propensities

Equation (2) was used to calculate the $P_{agg}$ for individual amino acids. $I^{pat}$ is not included in such a calculation since the pattern term for a residue is dependent upon that residue's position in the sequence.

Aggregation Propensity Profiles

The $P_{agg}$ values of individual amino acids were calculated over the length of a sequence. Eq (1) was used to calculate a $P_{agg}$ per residue, giving the full weight of $I^{pat}$ to any residue within a five-residue sequentially alternating hydrophobic-hydrophilic sequence. We then smoothed the $P_{agg}$ profile by averaging the resulting values over a sliding window of five residues and graphed according to central residue number. A sample $P_{agg}$ profile was created for PrP.

Detection of the Sensitive Regions

The regions of the sequence that are particularly prone to change the amyloid aggregation rates upon single mutations were identified as follows. The $P_{agg}$ profiles were calculated for the wt sequence and for every possible single mutant (20 amino acids possible for every residue). The values of these profiles at each residue were considered, and the highest and lowest possible $P_{agg}$ values at that residue are plotted along with the wt value without smoothing. Sensitive region profiles were calculated for AcP (pH 5), Aβ42 (pH 5), two SH3 domains (pH 2).

Results

Definition of the Intrinsic Aggregation Propensities:

The intrinsic propensity to form amyloid aggregates, $P_{agg}$, is defined by considering only the intrinsic factors (I):

$$P_{agg} = -0.08I^{hydr} + 0.96I^{pat} - 0.07I^{\alpha} + 0.08I^{\beta} - 0.47I^{ch} \quad \text{(Equation 2)}$$

$I^{hydr}$ represents the hydrophobicity of the sequence [Roseman, M. A. (1988). "Hydrophilicity of polar amino acid sidechains is markedly reduced by flanking peptide bonds." J Mol Biol 200(3): 513-22; and Cowan, R. and R. G. Whittaker (1990) "Hydrophobicity indices for amino acid residues as determined by high-performance liquid chromatography." Pept Res 3(2): 75-80, both hereby incorporated by reference]; $I^{pat}$ indicates the hydrophobic-hydrophilic patterning [Broome, B. M. and M. H. Hecht (2000) "Nature disfavors sequences of alternating polar and non-polar amino acids: implications for amyloidogenesis." J Mol Biol 296(4): 961-8 hereby incorporated by reference]; $I^{\alpha}$ measures the α-helical propensity [Munoz, V. and L. Serrano (1994) "Intrinsic secondary structure propensities of the amino acids, using statistical phi-psi matrices: comparison with experimental scales." Proteins 20(4): 301-11, hereby incorporated by reference]; $I^{\beta}$ is the β-sheet propensity [Street, A. G. and S. L. Mayo (1999) "Intrinsic beta-sheet propensities result from van der Waals interactions between side chains and the local backbone." Proc Natl Acad Sci USA 96(16): 9074-6, hereby incorporated by reference]; and $I^{ch}$ is the absolute value of the net charge of the sequence. Since pH influences three of these terms ($I^{hydr}$, $I^{pat}$, and $I^{ch}$), it should preferably be specified in order to solve Equation (2).

Table 5, below, gives Scales of hydrophobicity, β-sheet propensity and charge for the 20 natural amino acids,

TABLE 5

Scales of hydrophobicity, β-sheet propensity and charge for the 20 natural amino acids

| amino acid residue | Hydrophobicity (kcal mol$^{-1}$) [a] | β-sheet propensity[b] | charge[c] |
|---|---|---|---|
| Arg (R) | 3.95 | 0.35 | +1 |
| Lys (K) | 2.77 | 0.34 | +1 |
| Asp (D) | 3.81 | 0.72 | −1 |
| Glu (E) | 2.91 | 0.35 | −1 |
| Asn (N) | 1.91 | 0.40 | 0 |
| Gln (Q) | 1.30 | 0.34 | 0 |
| His (H) | 0.64 (2.87)[d] | 0.37 | 0 (+1)[d] |
| Ser (S) | 1.24 | 0.30 | 0 |
| Thr (T) | 1.00 | 0.06 | 0 |
| Tyr (Y) | −1.47 | 0.11 | 0 |
| Gly (G) | 0.00 | 0.60 | 0 |
| Pro (P) | −0.99 | n.d. | 0 |
| Cys (C) | −0.25 | 0.25 | 0 |
| Ala (A) | −0.39 | 0.47 | 0 |
| Trp (W) | −2.13 | 0.24 | 0 |

TABLE 5-continued

Scales of hydrophobicity, β-sheet propensity
and charge for the 20 natural amino acids

| amino acid residue | Hydrophobicity (kcal mol$^{-1}$)[a] | β-sheet propensity[b] | charge[c] |
|---|---|---|---|
| Met (M) | −0.96 | 0.26 | 0 |
| Phe (F) | −2.27 | 0.13 | 0 |
| Val (V) | −1.30 | 0.13 | 0 |
| Ile (I) | −1.82 | 0.10 | 0 |
| Leu (L) | −1.82 | 0.32 | 0 |

[a] hydrophobicity values of the 20 amino acid residues at neutral pH based on the partition coefficients from water to octanol. The data are from column 6 of Table 4.8 in ref. 30.
[b] β-sheet propensities of the 20 amino acid residues normalised from 0 (high β-sheet propensity) to 1 (low β-sheet propensity). The data are from column 4 of Table 1 of ref. 29. The β-sheet propensity of proline is not reported due to the difficulty in determining it experimentally. The β-sheet propensity of glycine is from theoretical calculations.
[c] values of charge are at neutral pH.
[d] values in brackets are at a pH lower than 6.0, when the histidine residue is positively charged The intrinsic aggregation propensity $P_{agg}$ is a dimensionless number, which may be scaled according to the factors in the above equation, and which may conveniently be chosen to give $P_{agg}$ values between −1 and +1 (−1 corresponding to reduced aggregation and +1 to enhanced aggregation).

Prediction of the Intrinsic Aggregation Propensities:

Since most studies of amyloid aggregation have been so far designed to detect fibril formation rather than to measure precisely aggregation rates, the conditions used varied considerably in different experiments and it is difficult to assess from the literature the intrinsic propensities of different sequences to aggregate. Equation 2 provides a natural separation between the intrinsic and the extrinsic factors that promote amyloid aggregation and therefore makes it possible to compare the intrinsic amyloid-forming propensities of different sequences. We ranked several intensely studied polypeptide sequences according to their intrinsic propensity to aggregate. Table 6 displays a list of disparate sequences and their aggregation propensities, calculated at pH 3 and pH 7.

TABLE 6

| sequence | pH 3 | pH 7 |
|---|---|---|
| Aβ40 | −0.03 | 0.79 |
| Aβ42 | 0.21 | 1.03 |
| ABri | −2.01 | 0.03 |
| AChE peptide (586-599) | −1.42 | 0.21 |
| AcP | −2.08 | 3.53 |
| amylin 1-37 | −0.27 | 0.40 |
| α-spectrin SH3 | −2.57 | 2.49 |
| PI3 SH3 | 0.34 | 0.98 |
| α-synuclein | −1.05 | −1.39 |
| β2 microglobulin | −0.26 | 7.80 |
| calcitonin | 0.53 | 1.48 |
| HypF | 0.71 | 6.99 |
| insulin | 3.85 | 5.09 |
| LRR | −0.55 | 0.28 |
| PrP | −0.73 | 10.13 |
| PrP peptide (106-126) | 0.87 | 1.54 |
| TTR | −3.41 | 1.12 |

It is important to consider the pH when calculating the amyloid aggregation propensity since pH influences the intrinsic factors $I^{hydr}$, $I^{pat}$, and $I^{ch}$. The set of sequences and data provides interesting results. Firstly, it is clear that at a low pH, most sequences actually have a low propensity to aggregate. Both the intrinsic propensity for aggregation and the stability of folded proteins decrease with the pH. Therefore amyloid fibrils may be obtained from folded proteins by lowering the pH, even if their intrinsic tendency to aggregate is reduced. At neutral pH, PrP, b2m, HypF, and insulin have the highest amyloid aggregation propensities, and they are known to form fibrils relatively easily. AcP also has very a high intrinsic aggregation propensity, and as a matter of fact this protein played and important role in establishing the principle that forming amyloid fibrils is a generic property of amino acid polymers. As expected, Aβ42 has a higher aggregation propensity than Aβ40 at both pH 3 and 7.

Intrinsic Aggregation Propensities of Individual Amino Acids:

The amyloid aggregation propensity of each amino acid can be calculated from Equation 2. The resulting scale is useful in designing mutations to increase or decrease amyloid aggregation. The scale at neutral pH is shown in Table 7 below, with the amino acids listed in decreasing order of propensity.

TABLE 7

| trp | 0.23 |
|---|---|
| leu | 0.21 |
| phe | 0.20 |
| gly | 0.17 |
| ile | 0.13 |
| tyr | 0.13 |
| met | 0.13 |
| ala | 0.12 |
| val | 0.12 |
| cys | 0.11 |
| his | (−0.57 if pH > 8.3) 0.06 (−0.61 if pH < 6.0) |
| ser | −0.01 |
| gln | −0.03 |
| asn | −0.03 |
| pro | −0.10 |
| thr | −0.12 |
| lys | −0.62 |
| glu | −0.64 |
| asp | (0.03 if pH < 4.3) −0.63 (0.05 if pH < 3.7) |
| arg | −0.72 |

At neutral pH, tryptophan, leucine, phenylalanine, and glycine have the highest amyloid propensity, while aspartic acid, lysine, glutamic acid, and arginine have the lowest. Interestingly, our scale assigns histidine a much lower amyloid aggregation propensity than the other aromatic residues, especially at lower pHs.

Aggregation Propensity Profiles

We can use Equation 2 to calculate the sum of the intrinsic factors (i.e. hydrophobicity, hydrophobic patterns, secondary structure propensities, and charge) individually for each residue in a polypeptide sequence. This operation results in a 'aggregation propensity profile', which illustrates how different regions of the sequence of a polypeptide have significantly different intrinsic propensities to aggregate.

Figure 7:
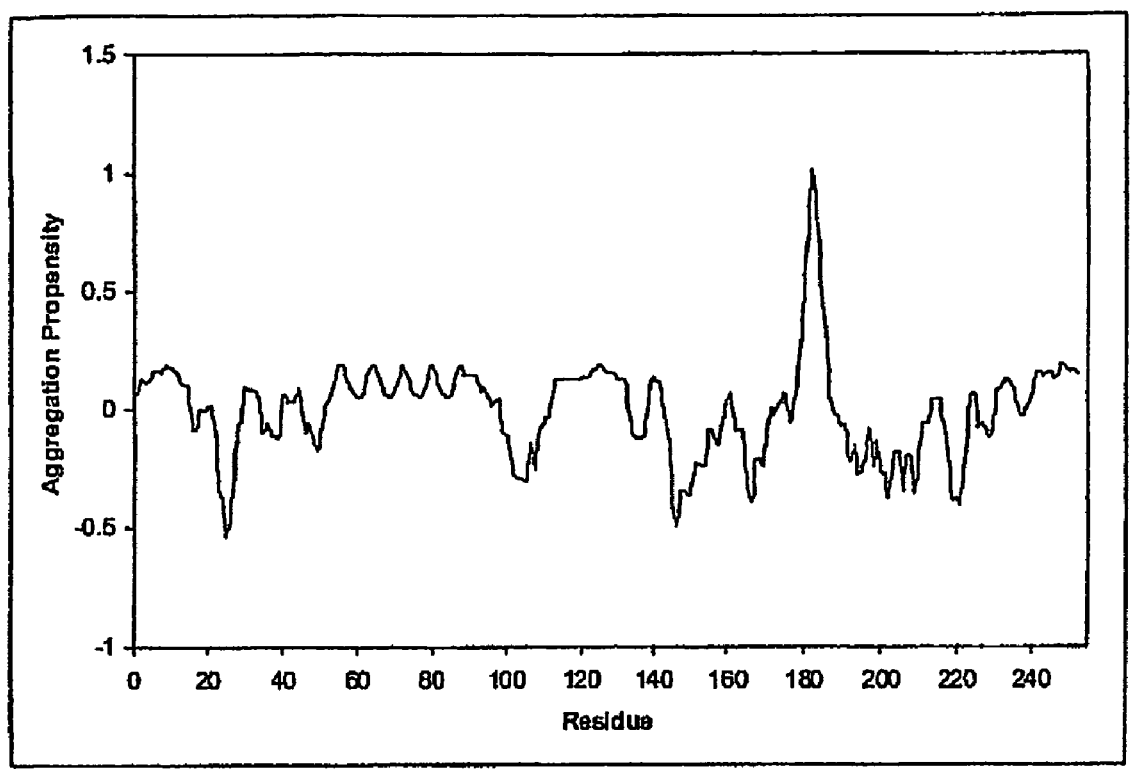
FIG. 7 shows amyloid aggregation propensity profile of PrP.

We first present the propensity profile for PrP. FIG. 7 shows amyloid aggregation propensity profile of PrP The amyloid aggregation propensity profile, pH 7, is shown along the sequence of PrP, calculated for each residue as if it were its own sequence from Eq (2) and averaged over a sliding window of five residues.

Residues 55-90 show a relatively high propensity towards aggregation. This is interesting, since additional repeats in this region are known to be linked to prion diseases. The region of amino acids 106-126, has a high propensity to aggregate, and it is known to form fibrils in vitro. However, the region that holds the most interesting feature of this profile runs from residue 180 to 190. Although some mutations in this region are known to be pathogenic, it would be interesting to see if different genetic variations in this region that lower the peak help protect their carriers from prion diseases. Known pathogenic mutations lie along some of the most interesting features of the profile, clustering around residues 105, 180, and 200.

Identification of the Sensitive Regions

Figure 8A:
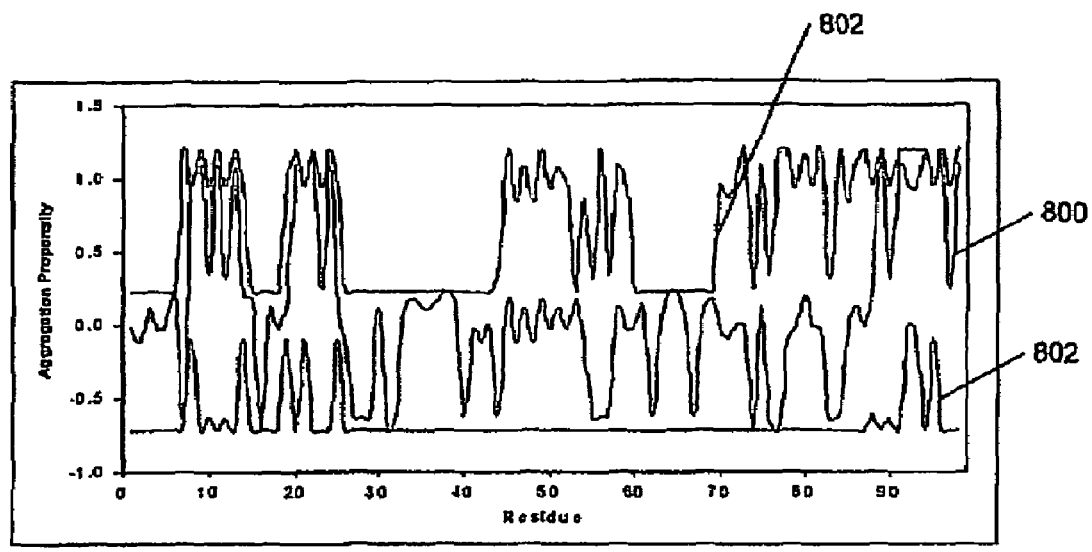
FIGS. 8a and 8b show AcP aggregation profile and sensitive regions.
Figure 8B:
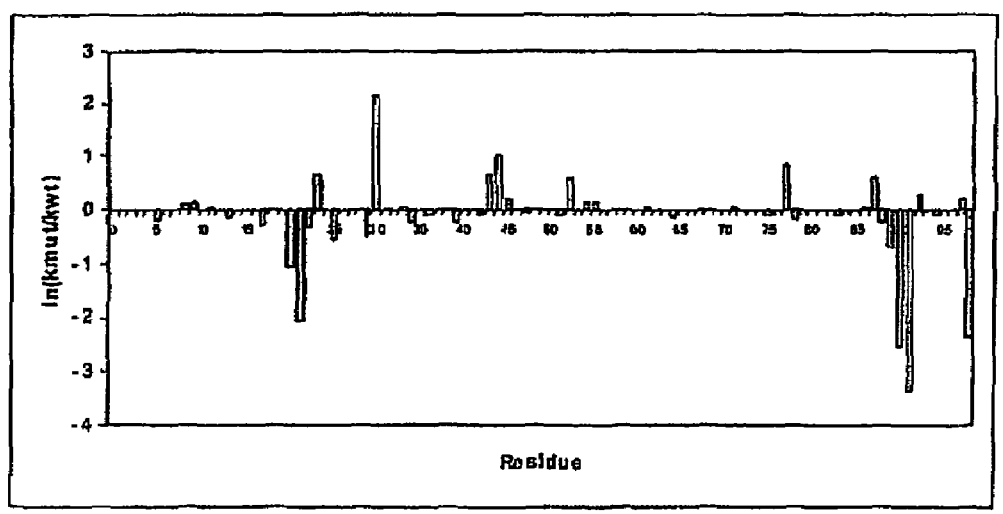
Figure 9A:
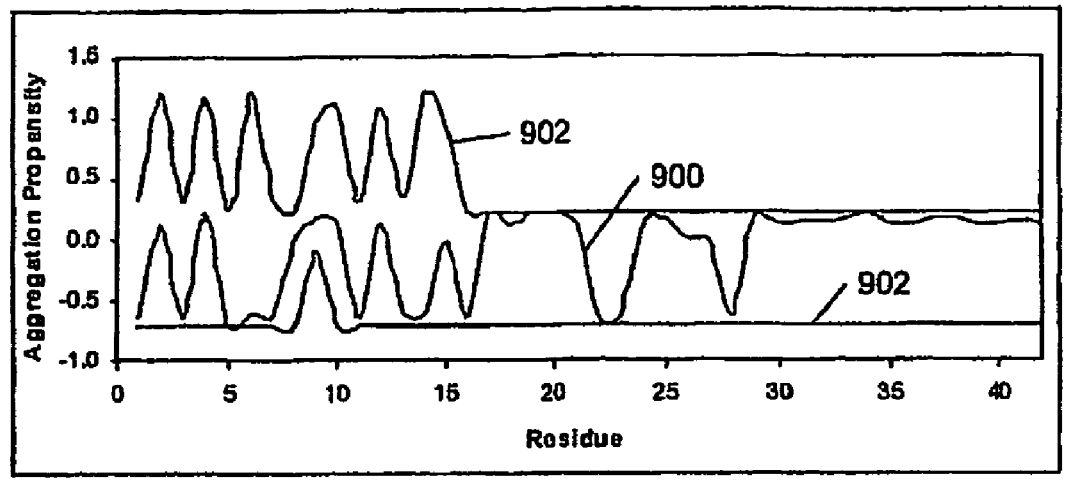
FIGS. 9a and 9b show Aβ42 aggregation profile and sensitive regions.
Figure 9B:
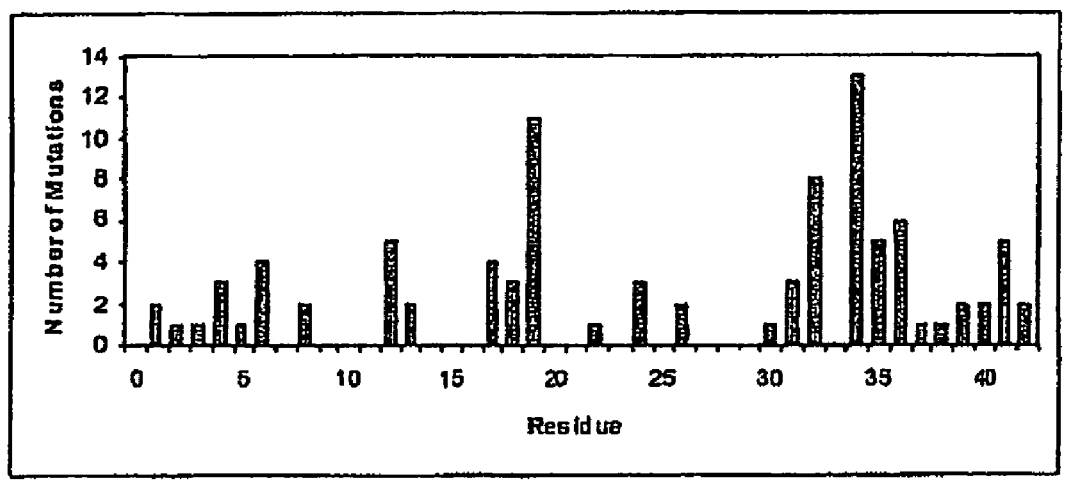
Figure 10A:
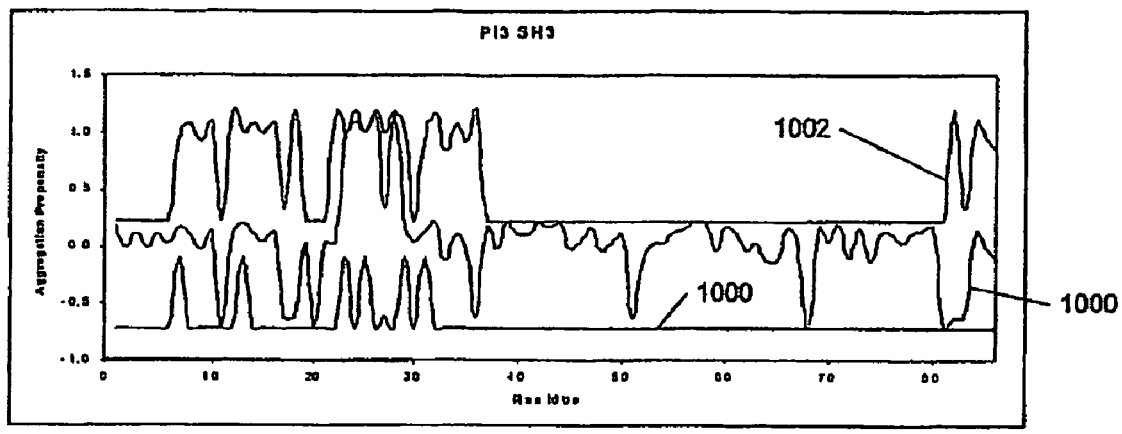
FIGS. 10a and 10b show PI3 SH3 and α-spectrin SH3 aggregation profiles and sensitive regions.
Figure 10B:
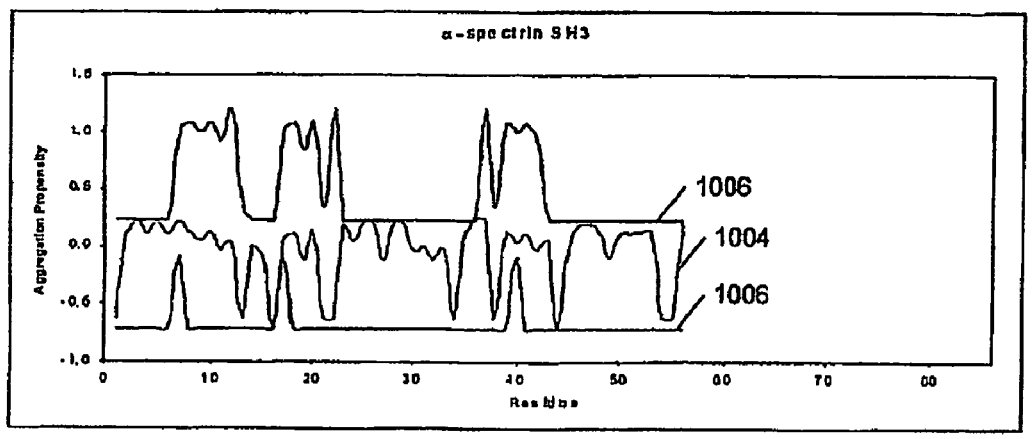

FIG. 8 shows AcP aggregation profile and sensitive regions. FIG. 8*a* shows the amyloid aggregation profile at pH 5.5 is shown for AcP. The wt profile is curve 800, and the highest and lowest possible propensity values for each residue are plotted in curve 802, all without smoothing. FIG. 8*b* shows the rate change as a result of various single mutations in AcP. Positive y-values indicate an increase in the aggregation rate. Experiments were performed at pH 5.5.

One of the most intriguing observations in recent amyloid kinetic studies is that the sequence of AcP seems to contain "sensitive" regions. Single amino acid mutations in these regions can change greatly the aggregation rates. These regions of the sequence appear to be particularly influential in the rate of amyloid formation (See FIG. 8*b*). An analysis of the propensity profiles offers new insight into the origin of these sensitive regions. At any given position along the sequence we calculated the propensity values for all possible single point mutants, thus obtaining the highest and lowest propensity values possible. By repeating this calculation for each position along the sequence can thus construct two new profiles, of maximal and minimal propensities, respectively. These two profiles are compared with the profile for the wt sequence to display the range of available increases and decreases at each position.

We applied this type of analysis to three polypeptide sequence for which extensive mutational data on aggregation rates is available: AcP, Aβ42, and two domains of SH3. The pH of each profile was chosen to allow the best comparison with available experimental data.

AcP: The aggregation propensity profile for AcP was calculated at pH 5.5 for the wt sequence (FIG. 2A, pink) and plotted with the highest and lowest propensities profiles (FIG. 2A, blue). The results are compared with an experimental kinetic study of 55 AcP single-substitution mutants, also done at pH 5.5 (FIG. 2B) [Chiti 2002a,b]. Interestingly, the two regions (residues 16-31 and 87-98 [Chiti 2002a]) of AcP which have been identified as sensitive have regions of high propensity in the wt sequence. Even more interestingly, increases and decreases in the aggregation rates of the majority of AcP mutations can be observed as areas of high potential change between the wt aggregation profile and the highest or lowest potential profiles. The one major exception is the increase for the A30G mutant. However, as this mutant is located in the centre of an α-helix. Since experiments were performed in 25% TFE, which stabilizes helices, it is likely that this discrepancy is due to a residual stability that is not considered in our formula, which is designed to deal only with destabilized polypeptides.

FIG. 9 shows Aβ42 aggregation profile and sensitive regions. FIG. 9*a* shows the amyloid aggregation profile at pH 5 is shown for Aβ42. The wt profile is plotted in curve 900, and the highest and lowest possible propensity values for each residue are plotted in curve 902, all without smoothing. FIG. 9*b* shows the frequency of a random mutation at each residue for 36 least-aggregating sequences as determined by Wurth et al. [Wurth, C., N. K. Guimard and M. Hecht. (2002) "Mutations that reduce aggregation of the Alzheimer's Abeta42 peptide: an unbiased search for the sequence determinants of Abeta amyloidogenesis." J Mol Biol 319(5): 1279-90].

Aβ42: The aggregation propensity profile for Aβ42 was calculated for the wt sequence (FIG. 9*a*, curve 900) and plotted with the highest and lowest propensities profiles (FIG. 9*a*, curve 902). The first feature to note in the Aβ42 wt profile is the high propensity around residues 32-42. Recent work by Petkova et al. provides a structural model of the Aβ fibril at the residue level [Petkova, A. T., Y. Ishii, et al. (2002). "A structural model for Alzheimer's beta-amyloid fibrils based on experimental constraints from solid state NMR." Proc Natl Acad Sci USA 99(26): 16742-7]. Their results place the residues 28-42 directly in the β-sheet core of the amyloid fibril. Additionally, residues 15-24 are able to form fibrils in vitro, again a region of high wt aggregation propensity. In fact, residue 22, 23, and 28 are the only residues from 17-42 that are not maximized for amyloid propensity. This is particularly interesting since a number of pathogenic mutations have been identified at residue 22. To further compare the results of this analysis with experimental work, we looked at a recent in vivo study on Aβ42 by Wurth et al. [ibid]. Aβ42 was linked to green fluorescent protein (GFP), subjected to random mutation, and expressed in cell colonies. GFP fluorescence quenches upon Aβ42 amyloid aggregation. The 36 most fluorescent (i.e. least aggregating) colonies were then chosen for Aβ42 sequencing [Wurth 2002]. FIG. 3B displays a histogram of the number of times each residue was mutated in the 36 least aggregating mutants. Since the in vivo pH cannot be precisely known, we calculated the aggregation propensity profiles over a range of pH, from pH 2 to pH 9. FIG. 3A displays the result of the pH 5 calculation, but the profiles are only weakly dependent on values of pH in the range from 4.5 to pH 9. It is clear to see that the regions which are calculated to have the greatest potential for reducing the aggregation propensity are indeed those regions where the most mutations randomly occurred in the Wurth et al. study. Considering the complications of an in vivo system as well as changes in $P_{agg}$ due to the linked GFP, these are excellent results.

FIG. 10 shows PI3 SH3 and α-spectrin SH3 aggregation profiles and sensitive regions. The amyloid aggregation profiles of SH3 are at pH 2. The wt profiles are plotted in curves 1000, 1004, while the highest and lowest possible propensity values for each residue are plotted in curves 1002, 1006, all without smoothing. FIG. 10*a* displays the PI3 profiles, and FIG. 10*b* the α-spectrin profiles.

SH3: The aggregation propensity profiles for PI3-SH3 (FIG. 4A) and α-spectrin SH3 (FIG. 4B) were calculated for the wt sequences (curves 1000, 1004) and compared with the highest and lowest propensity profiles (curves 1002, 1006). The SH3 domain of PI3 has been studied as a non-pathogenic amyloid-forming globular protein. The native state of SH3 is highly stable and the protein must be denatured before amyloid fibrils could form. Since the conditions used are often highly acidic to counter the stability, profiles were determined pH 2. While most SH3 domains, including α-spectrin SH3, have excellent consensus at residues 25 and 26, typically Lys25-Lys26, PI3-SH3 has the atypical residues His25-Leu26; α-spectrin SH3, containing the Lys25-Lys26 residues does not form detectable fibrils after an incubation of 30 days, while PI3 SH3 does. Substitutions of these two lysine residues into PI3 SH3 makes its fibril formation undetectable as well, whereas substituting residues 20-26 from PI3-SH3 into α-spectrin SH3 enables fibril formation over this time scale. These experiments were all carried out under highly acidic conditions. In comparing the aggregation profiles of the two wt sequences at low pH (FIG. 4), the $P_{agg}$ values of residues 20-26 are significantly less for α-spectrin SH3 than for PI3-SH3, corresponding well with the experimental observations.

We have presented here method to calculate intrinsic amyloid aggregation propensities for a number of sequences of interest in amyloid research. We have also presented an amyloid propensity scale for individual amino acids, which may be used in designing mutants with controlled aggregation propensities. Additionally, we have calculated propensity profiles to examine amyloidogenic features of five polypeptides, PrP, AcP, Ab42, PI3 SH3, and α-spectrin SH3. These profiles offer a new understanding of experimental observations on these sequences.

The following abbreviations have been employed: Aβ=Alzheimer's β-peptide; AChE=acetylcolinesterace; AcP=acetylphosphatase; HypF=N-terminal domain of prokaryotic protein HypF; LRR=leucine rich repeats; PI3=phosphatidylinositol 3-kinase; PrP=prion protein; TTR=transthyretin; GFP=green fluorescent protein.

Patterning—Further Information

This section provides further information on patterns usable in prediction methods based upon equations 2 (above) and 3 (below).

Alternating patterns are among the least common sequence patterns in nature and are able to determine secondary structural motifs in designed proteins. Patterns of five alternating hydrophilichydrophobic residues, where the residues with hydrophobicity values $\leq -0.5$ on the Roseman scale [Roseman, M. A., *Hydrophilicity of polar amino acid side-chains is markedly reduced by flanking peptide bonds.* J Mol Biol, 1988. 200(3): p. 513-22] were considered hydrophobic and those with values $\geq 0.5$ hydrophilic. Patterns of five residues were chosen because appears to be the minimum number of alternating residues that can differentiate between β-sheet promoting (•Δ•Δ•) and α-helix promoting (•Δ•ΔΔ) patterns. One way of representing these patterns is to add +1 to the pattern term for each five-residue alternating sequence found in a sequence. This representation results in a correlation coefficient of 0.47 when used alone to predict the absolute rates of AcP sensitive region mutants. This may be refined by 1) adding less-weighty contributions for four- and three-residue alternating patterns, 2) adding negative values of various weights for a five-residue pattern matching the α-helical promoting pattern, and 3) adding contributing terms for consecutive hydrophilic or consecutive hydrophobic residues. However, none of the above adjustments appear to provide a significant improvement upon the simple representation of a +1 value for each five-residue alternating pattern found in the sequence, at least for the dataset studied.

The approximately 20 amino acids which may be categorised as hydrophilic (charged residue or polar residue, for example serine or cystine) or hydrophobic (non-polar) according to the above definition. The terms (and categorisation) non-polar and polar may be employed, although "hydrophilic" may include either or both of "polar" and "charged".

Alternatively a categorisation as shown below may be employed:
hydrophobic: ala, val, phe, ile, leu, met, tyr, trp (some authors include tyr and trp as polar, but attending to their general character they are quite hydrophobic)
charged: asp, glu, lys, arg, his (some authors place his as polar)
polar: ser, thr, cys, gln, asn.
glycine: can be hydrophobic or may be classified as an independent glycine being considered neutral residue.

It has been determined experimentally that certain patterns of amino acids, in particular patterns of hydrophilic ("P")/hydrophobic ("NP") amino acids result in an increased propensity to aggregate. More particularly, alternating patterns give rise to an increased propensity to aggregate, in particular alternating patterns having a length of five or more amino acids (although some sequences of three or more may show a small effect). Thus, for example, NP P NP P NP and P NP P NP P are examples of length five alternating patterns giving rise to increased aggregation propensity. Other patterns may inhibit aggregation, for example a string of hydrophilic amino acids, or a string of some particular amino acids such as prolines.

The effects of these patterns are taken into account in equation 2 above and equation 3 below in the term $I^{pat}$, in one embodiment $I^{pat}$ being given a value of +1 for each alternating pattern found in the sequence. However it will be appreciated that the increment given to $I^{pat}$ for each identified pattern is essentially arbitrary, being scaled by its multiplying factor in the equation. The skilled person will recognise that $I^{pat}$ may be adjusted by a first value for a first pattern and a second value for a second pattern, for example +1 for a length 5 alternating string of amino acids, and +2 for, say, a length 9 alternating string of amino acids. Optionally $I^{pat}$ may be adjusted by a negative value, say −1, for an aggregation inhibiting pattern. Again it will be recognised that although only one $I^{pat}$ term has been included in equation 2 above, more than one $I^{pat}$ term may be included, each with a separate multiplying factor. (Interestingly, alternating sequences as mentioned above which have a tendency to aggregate appear not to be well represented in nature, perhaps because they are unfavourable and have been selected out during evolution.)

Computer System for Implementing Embodiments of the Invention

Computer system 300 may also be employed to implement equation 2 above, for example when running program code to implement the flow chart of FIG. 6, and also equation 3 below, in accordance with the flow chart of FIG. 11 and Example 7, which describes embodiments of the present invention.

Figure 6:
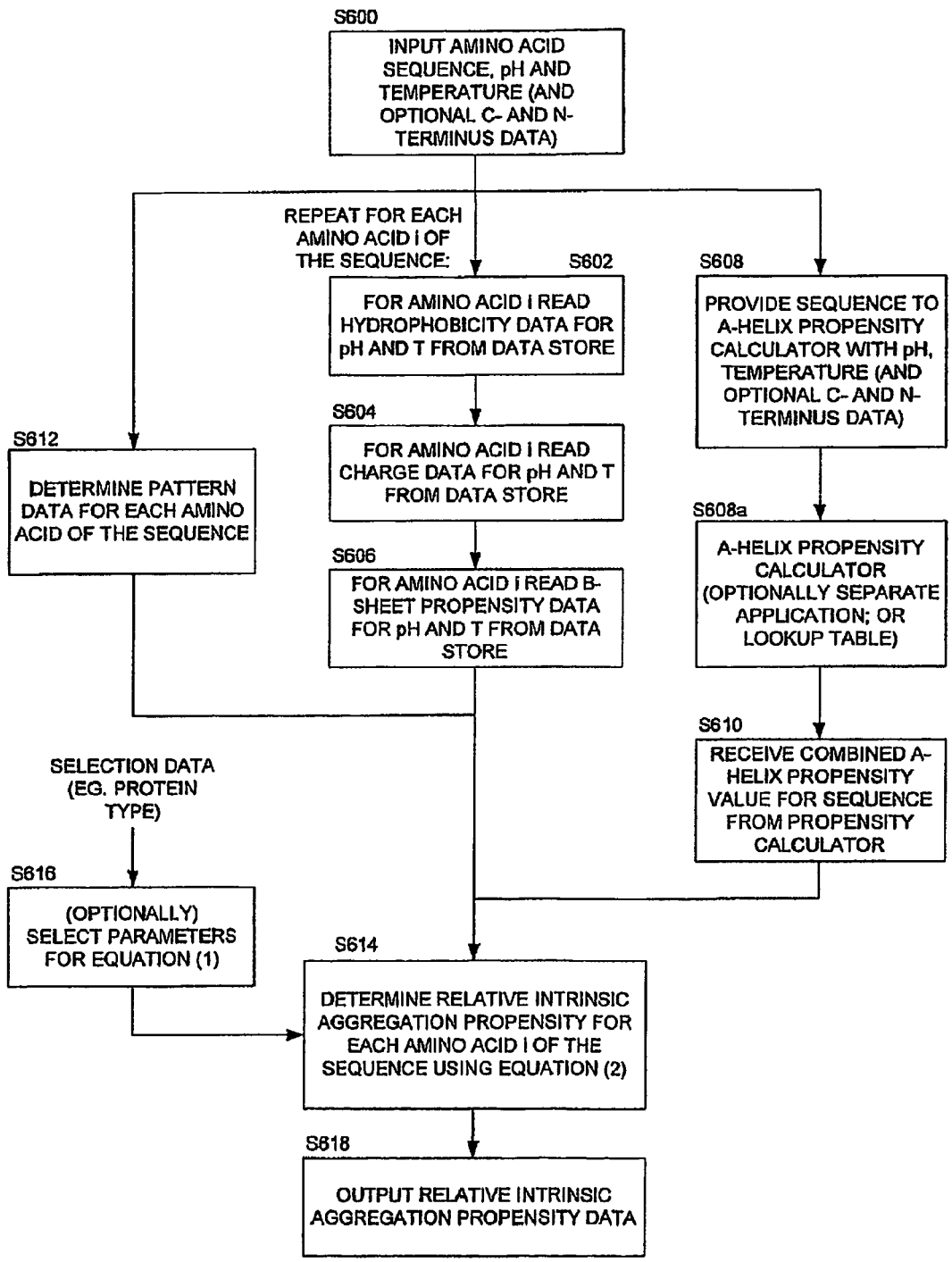
FIG. 6 shows a flow chart of a procedure for determining relative intrinsic aggregation propensity.

FIG. 6 shows a flow chart of a procedure for determining relative intrinsic aggregation propensity as described above, using equation 2. Many of the steps of FIG. 6 are similar to those previously described with reference to FIG. 4. Thus at step s600 an amino acid sequence, together with pH and temperature data (for determining charge and helical propensity) are input and then at steps s602, s604 and s606 the procedure determines, for each amino acid i of the sequence, a hydrophobility, charge, and β-sheet propensity for the amino acid. At step s608 the sequence data is also provided to an α-helix propensity calculator, together with the pH and temperature values input at step s600. At step s608a an α-helix propensity calculator determines an α-helix propensity value for each amino acid in the sequence and, at step s610, this is received by the program code for subsequent use at step s614. The α-helix propensity may be calculated by the procedure by simply looking up a propensity value for each amino acid of the sequence in a table of propensity values for each of the 20 or so amino acids. (The look-up table approach may also be used with the procedure of FIG. 4). Alternatively an α-helix propensity calculator program may be used to determine an α-helix propensity value for each amino acid, as described with reference to FIG. 4 above. Preferably (but not essentially) pH and temperature are provided to the α-helix propensity determining code.

At step s612 pattern data for each amino acid of the sequence is determined. As the skilled person will appreciate there are many ways in which this may be done, for example counting the number of polar/non-polar alternations until this reaches 5 or more and then allocating a pattern data value ($I^{pat}$) of, say, +1 to each amino acid in the alternating sequence (alternatively these values could be normalised such that, say, each amino acid in an alternating sequence of length 5 has a value of +0.2).

Optionally, at step s616, a set of parameters may be selected for equation 2 based upon a type or group of proteins to which it is desired to apply the equation, for example ACP and the like.

At step s614 all the data for equation 2 is available for each amino acid of the sequence and this equation is applied to determine a relative intrinsic aggregation propensity value for each amino acid. This data is then output at step s618, for example as a data file and/or as a (printed) matrix, as a graph, and/or in some other manner. Figures . . . (FIGS. 2-4 of the paper) show examples of graphical outputs; if desired averaging over a small number of amino acids (say 2 to 10 amino acids) may be employed to smooth the curve. Optionally further processing may be employed to identify sensitive regions as above. Thus, broadly speaking, the relative intrinsic aggregation propensities for each amino acid of a wild type sequence may be summed and then at each position in the sequence a separate sum may be determined for each of the 20 or so possible single point mutations to determine those positions in which a mutation is potentially more likely to result in or contribute to an enhanced aggregation rate. If desired the results of such a procedure can, again, be output graphically (and/or in the other ways mentioned above), as also shown in FIGS. 7 to 10).

Example 7

Predicting Absolute Amyloid Aggregation Rates of Polypeptide Chains

Here we describe an equation that builds upon and extends the procedure of Example 6 and uses the knowledge of the amino acid sequence and of the experimental conditions to reproduce, with, in embodiments, a correlation coefficient of 0.92, in vitro aggregation rates of peptides or denatured proteins. These results indicate that the formation of amyloid aggregates can be rationalised in terms of simple physico-chemical principles. The described technique is able to predict, over a broad range of potential experimental conditions, the aggregation rates of a number of non-homologous unstructured peptides and unfolded or partially unfolded proteins.

We introduce the following phenomenological formula to describe the absolute aggregation rates of polypeptide chains:

$$\ln(k) = \alpha_0 + \alpha_{hydr}I^{hydr} + \alpha_{pat}I^{pat} + \alpha_\alpha I^\alpha + \alpha_\beta I^\beta + \alpha_{ch}I^{ch} + \alpha_{pH}E^{pH} + \alpha_{ionic}E^{ionic} + \alpha_{conc}E^{conc}$$ Equation (3)

where ln(k) is the natural logarithm of the aggregation rate k, in s$^{-1}$. Factors intrinsic to the amino acid sequence are denoted with I, while extrinsic, condition-dependent factors are denoted with E. $I^{hydr}$ represents the hydrophobicity of the sequence, taken as the sum of the hydrophobic contributions of each residue from the Roseman scale, using the Cowan scale at pH 3.4 to estimate the changes with pH [Roseman, M. A., *Hydrophilicity of polar amino acid side-chains is markedly reduced by flanking peptide bonds*. J Mol Biol, 1988. 200(3): p. 513-22; Cowan, R. and R. G. Whittaker, *Hydrophobicity indices for amino acid residues as determined by high-performance liquid chromatography*. Pept Res, 1990. 3(2): p. 75-80.]. $I^{pat}$ corresponds to the existence of patterning of alternating hydrophobic-hydrophilic residues; a factor +1 was assigned for each pattern of five consecutive alternating hydrophobic and hydrophilic residues in the sequence [Broome, B. M. and M. H. Hecht, *Nature disfavors sequences of alternating polar and non-polar amino acids: implications for amyloidogenesis*. J Mol Biol, 2000. 296(4): p. 961-8.]. $I^\alpha$ measures the overall α-helical propensity of the sequence, taken as the sum of the natural logarithms of the intrinsic α-helical propensities of each residue [Munoz, V. and L. Serrano, *Intrinsic secondary structure propensities of the amino acids, using statistical phi-psi matrices: comparison with experimental scales*. Proteins, 1994. 20(4): p. 301-11]. $I^\beta$ is the β-sheet propensity, calculated as the sum of the natural logarithm of the intrinsic β-sheet propensity of each residue; we assigned a value of 1% to proline (β-sheet breaker), although results were not affected when values of up to 20% were considered; we assigned a value of 50% to glycine (undetermined) [Street, A. G. and S. L. Mayo, *Intrinsic beta-sheet propensities result from van der Waals interactions between side chains and the local backbone*. Proc Natl Acad Sci USA, 1999. 96(16): p. 9074-6]. $I^{ch}$ is the absolute value of the net charge of the sequence. $E^{pH}$ is the pH of the solution in which aggregation occurs and $E^{ionic}$ is the ionic strength of the solution, given in millimolar units. Finally, $E^{conc}$ is the measure of polypeptide concentration C in the solution, taken in the form of ln(C+1), with C in millimolar units.

The dataset used to determine and test the prediction algorithm comprised both data from the extensive mutational study on AcP and data on other systems available in the literature—see Table 8 below.

TABLE 8

| sequence | mutants | pH | ionic strength | [peptide] | references |
|---|---|---|---|---|---|
| AcP | 59 | 5.5 | 43 mM | 0.04 mM | [27, 31, 50] |
| Aβ40 | 2 | 7.4 | 150 mM | 0.25 mM | [53] |
| Aβ40 | none | 7.4 | 81 mM | 0.03 mM | [59] |
| Aβ42 | none | 7.4 | 81 mM | 0.01 mM | [59] |
| ABri | none | 9.0 | 89 mM | 1.31 mM | [55] |
| AChE peptide 586-599 | none | 7.0 | 7.7 mM | 0.20 mM | [58] |
| Amylin 1-37 | 2 | 7.2 | 1.1 mM | 2.0 mM | [51] |
| Amylin 1-37 | none | 7.3 | 1.4 mM | 0.14 mM | [56] |
| Amylin 8-37 | none | 7.3 | 1.4 mM | 0.14 mM | [56] |
| HypF domain | none | 5.5 | 40 mM | 0.08 mM | [62] |
| IAPP precursor | none | 5.0 | 0.1 mM | 0.001 mM | [57] |
| LRR | 1 | 7.8 | 3.3 mM | 0.39 mM | [54] |
| PrP peptide 106-126 | 3 | 5.0 | 1.2 mM | 0.33 mM | [52] |
| TTR | 3 | 4.4 | 130 mM | 0.014 mM | [43] |

References for the above table are as follows:

27. Chiti, F., et al., *Studies of the aggregation of mutant proteins in vitro provide insights into the genetics of amyloid diseases*. Proc Natl Acad Sci USA, 2002b. 99 Suppl 4: p. 16419-26.

31. Chiti, F., et al., *Kinetic partitioning of protein folding and aggregation*. Nat Struct Biol, 2002a. 9(2): p. 137-43.

43. Hammarstrom, P., et al., *Sequence-dependent denaturation energetics: A major determinant in amyloid disease diversity*. Proc Natl Acad Sci USA, 2002. 99 Suppl 4: p. 16427-32.

50. Calamai, M., et al., *Relative Influence of Hydrophobicity and Net Charge in the Aggregation of two Homologous Proteins*. Biochemistry, 2003. submitted.

51. Azriel, R. and E. Gazit, *Analysis of the minimal amyloid-forming fragment of the islet amyloid polypeptide. An experimental support for the key role of the phenylalanine residue in amyloid formation.* J Biol Chem, 2001. 276(36): p. 34156-61.
52. Salmona, M., et al., *Molecular determinants of the physicochemical properties of a critical prion protein region comprising residues 106-126.* Biochem J, 1999. 342 (Pt 1): p. 207-14.
53. Miravalle, L., et al., *Substitutions at codon 22 of Alzheimer's abeta peptide induce diverse conformational changes and apoptotic effects in human cerebral endothelial cells.* J Biol Chem, 2000. 275(35): p. 27110-6.
54. Symmons, M. F., et al., *X-ray diffraction and far-UV CD studies of filaments formed by a leucine-rich repeat peptide: structural similarity to the amyloid fibrils of prions and Alzheimer's disease beta-protein.* FEBS Lett, 1997. 412(2): p. 397-403.
55. El-Agnaf, O. M., et al., *Effect of the disulfide bridge and the C-terminal extension on the oligomerization of the amyloid peptide ABri implicated in familial British dementia.* Biochemistry, 2001. 40(12): p. 3449-57.
56. Goldsbury, C., et al., *Amyloid fibril formation from full-length and fragments of amylin.* J Struct Biol, 2000. 130 (2-3): p. 352-62.
57. Kayed, R., et al., *Conformational transitions of islet amyloid polypeptide(IAPP) in amyloid formation in vitro.* J Mol Biol, 1999. 287(4): p. 781-96.
58. Cottingham, M. G., M. S. Hollinshead, and D. J. Vaux, *Amyloid fibril formation by a synthetic peptide from a region of human acetylcholinesterase that is homologous to the Alzheimer's amyloid-beta peptide.* Biochemistry, 2002. 41(46): p. 13539-47.
59. Fezoui, Y. and D. B. Teplow, *Kinetic studies of amyloid beta-protein fibril assembly. Differential effects of alpha-helix stabilization.* J Biol Chem, 2002. 277(40): p. 36948-54.
62. Chiti, F., et al., *Solution conditions can promote formation of either amyloid protofilaments or mature fibrils from the HypF N-terminal domain.* Protein Sci, 2001. 10(12): p. 2541-7.

Aggregation rates for AcP and TTR variants were determined under conditions that promote the unfolding of the native state into an ensemble of unfolded or partially unfolded conformations. This allowed us to examine factors favouring amyloid formation excluding any involvement of changes in the stability of the native state that might occur as a consequence of the mutations. Since the remaining sequences are all peptides that do not fold into a defined globular structure we can use kinetic data from buffered solutions while remaining confident that the changes in aggregation rates reported in the literature are not due to modification in native state structure.

We first determined (see Methods) the coefficients $\alpha$ given in Eq (3) by fitting them from the experimental ln(k) values for the proteins, peptides and their mutants as reported in Table 8. The values reported in Table 9 below represent our best estimates of these parameters. Table 9 also displays their statistical significance (p-value).

TABLE 9

|  | $\alpha$ | p-value |
| --- | --- | --- |
| intercept | −8.2 |  |
| hydrophobicity | −0.08 | 0.005 |
| pattern | 0.96 | <0.001 |
| $\alpha$-helix | −0.07 | 0.060 |
| $\beta$-sheet | 0.08 | 0.031 |
| charge | −0.47 | <0.001 |
| pH | −0.22 | 0.284 |
| ionic concentration | −0.03 | <0.001 |
|  | 3.05 | <0.001 |

Figure 11:
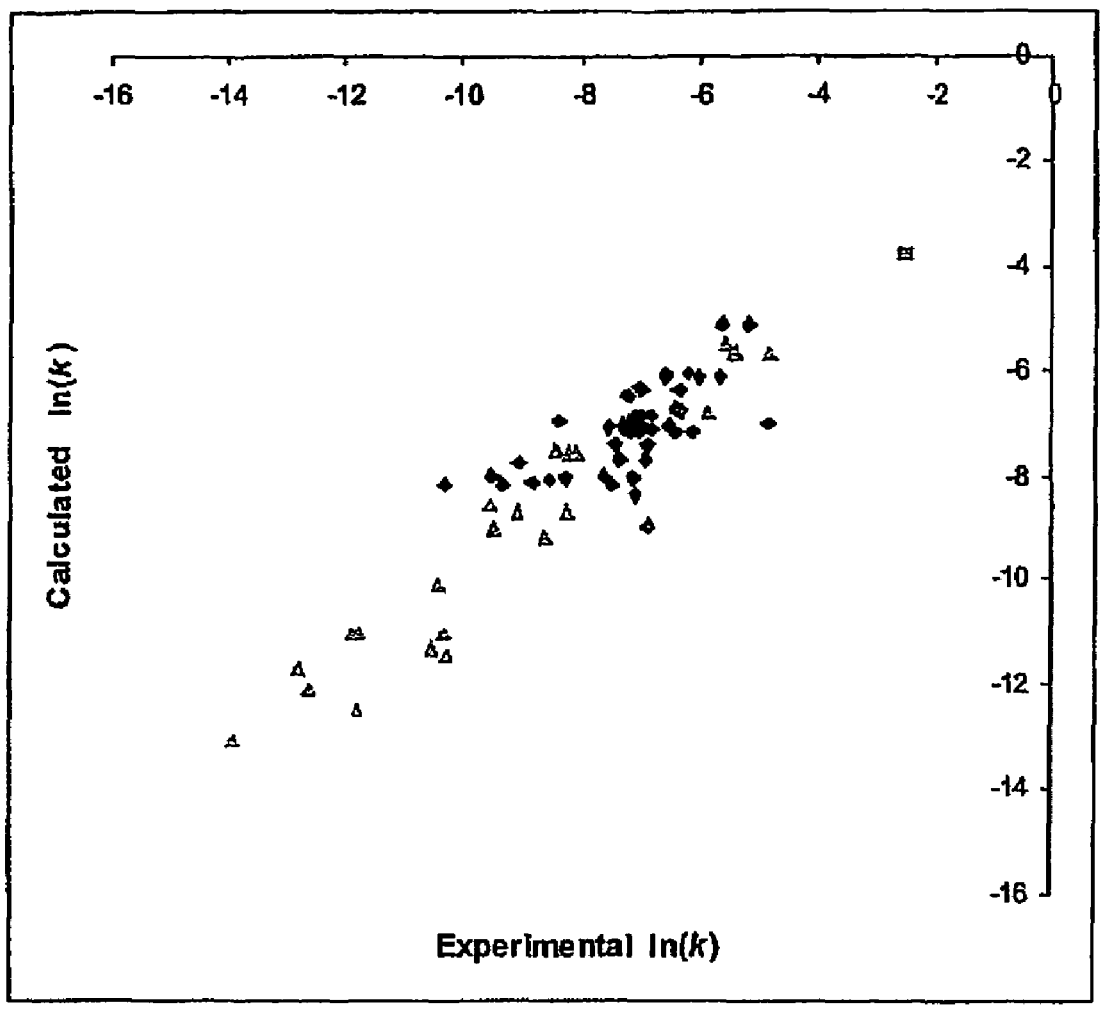
FIG. 11 shows a graph of calculated (logarithm) absolute aggregation rates against experimentally determined rates.

FIG. 11 shows results from the regression analysis run on the entire dataset, which compares the calculated and observed aggregation rates for various sequences. The calculated values for ln(k), determined using Equation (3) and the coefficients $\alpha$ reported in Table 9, are plotted against the experimental values. Data for wild-type AcP and its mutants or variants are shown in diamonds, while data for the other sequences in the dataset are shown in triangles. The comparison between the predicted and the experimental aggregation rates for the N-terminal domain of HypF is plotted as a square. The linear correlation coefficient of the calculated and observed values for the entire dataset is 0.92 (p<0.0001). The root mean squared error between the calculated and observed ln(k) values was 0.7; this value is an estimate of the statistical error on the prediction of ln(k), consistent with the results obtained by the bootstrapping test (see below).

Validation of the Predictions

In order to test the accuracy and predictive power of Eq (3) for determining the aggregation rates of polypeptide chains we used two cross-validation methods, a bootstrapping procedure [Press, W. H., et al., *Modeling of Data.* Numerical Recipes in C++, 2002 (Cambridge University Press): p. 696-697], and a jackknife method [Mardia, K. V., J. T. Kent, and J. M. Bibby, *Multivariate Analysis.* Academic Press London, 1979].

In the bootstrapping test, we randomly divided the entire dataset into two subsets. The first set, composed of two-thirds of the sequences, was used as the training set, from which the $\alpha$ coefficients were estimated. These coefficients were then used to predict the aggregation rates of the remaining sequences, the test set. The procedure was repeated 25 times, each time with a different random choice of the training set. The distribution of the correlation coefficients between the predicted and the experimental values was plotted for the training and test sets.

Figure 12A:
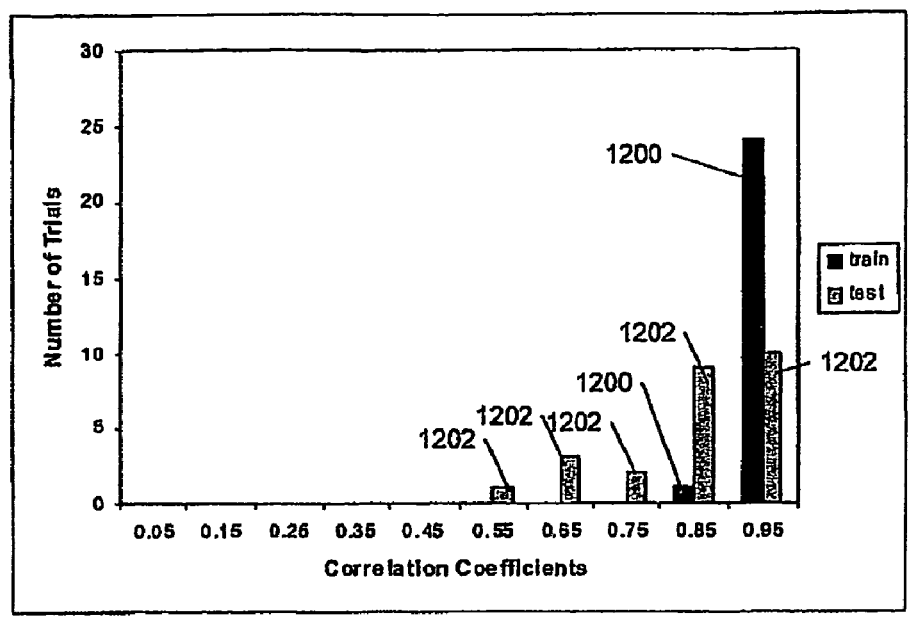
FIGS. 12a and 12b show, respectively, a distribution of correlation coefficients for absolute aggregation rate determination, and a graph of predicted (logarithm) absolute aggregation rates against experimentally determined rates.

FIG. 12a shows results from the bootstrapping test for Equation (3). The histogram shows the distribution of the correlation coefficients of both training 1200 and test 1202 sets for the 25 trials. The correlation coefficient for the training set ranged from 0.89 to 0.94 with a peak at 0.92. The p-value is lower than 0.0001 in all cases. The correlation coefficient for the test set ranged from 0.50 to 0.94 with a peak at 0.84. We obtained correlation coefficients lower than 0.70 in only four cases. An inspection of the training sets used in these cases revealed that the random selection had excluded an entire set of experimental data (data corresponding to measurements performed under the same experimental conditions), making the fitting of the factors dependent solely on experimental conditions, i.e. the extrinsic parameters E, somewhat inaccurate.

We then adopted the jackknife cross-validation method, in which a rate for each sequence is predicted in turn after having left that particular sequence aside (as well as any sequences corresponding mutants of that original polypeptide) during the determination of the best α coefficients for the remaining sequences. We performed this procedure for all of the wild-type and mutated polypeptides reported in Table 8; the experimental conditions for each observed rate are reported in Table 8. The linear correlation coefficient between predicted and observed rates was 0.88 in this case. The results of this test for the non-homologous wild-type sequences in our dataset are shown in FIG. 12b.

Figure 12B:
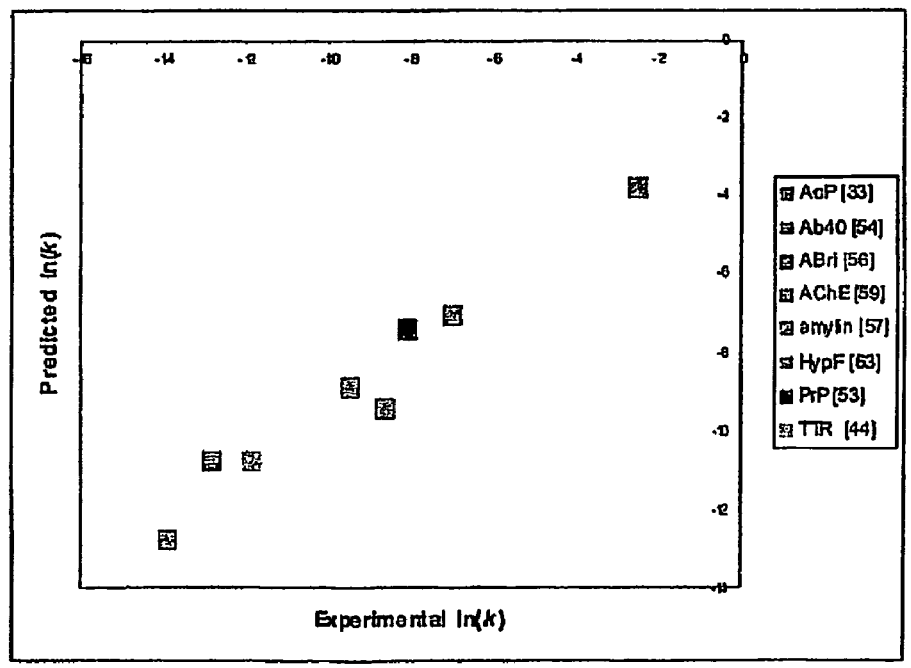

FIG. 12b shows ln(k) values predicted for all the non-homologous wild-type sequences in our dataset by means of the jackknife cross-validation analysis. Predicted values of ln(k) for each of the wild type sequences shown were calculated using a regression analysis on the data for all the sequences in the dataset except the data for the single wild type sequence predicted. The relatively good agreement between the predicted and experimental aggregation rates for the various proteins and peptides examined in this study shows the reliability of the formula in determining absolute aggregation rates from unstructured states.

A compelling test for our formula is the prediction of the aggregation rate of the N-terminal domain of prokaryotic globular protein HypF. This 91-residue polypeptide chain has been shown to form amyloid fibrils under conditions similar to those used in the AcP studies. HypF forms amyloid fibrils even more rapidly than AcP, which has one of the fastest amyloid aggregation rates in the dataset used. We predict ln(k)=−3.8 for HypF using Eq (3). An experimental bound for the rate of aggregation is ln(k)≧−2.5 The comparison between predicted and observed aggregation rates of HypF (see FIG. 11) shows that both values are significantly faster than any other rate in our dataset.

Influence of Individual Factors

The values of the coefficients α that we determined enable us to explore the influence of different factors on the propensity of a sequence to form amyloid aggregates.

Intrinsic Factors

Hydrophobicity. Hydrophobic interactions have long been suggested to play a significant role in amyloid formation. The hydrophobicity scale that we used assigns positive values to hydrophilic residues and negative values to hydrophobic residues [Roseman, M. A., *Hydrophilicity of polar amino acid side-chains is markedly reduced by flanking peptide bonds.* J Mol Biol, 1988. 200(3): p. 513-22; Creighton, T. E., 4.2.3 *Aqueous Solutions*, in *Proteins. Structure and molecular properties*. 1993, W.H. Freeman & Co.: New York. p. Table 4.8, column 6]. As we found a significant (p=0.005) negative coefficient (−0.08) for $I^{hydr}$, our analysis confirms the importance of the effect of hydrophobicity on aggregation. As the hydrophobicity increases, $I^{hydr}$ becomes more negative, leading to a positive contribution to ln(k), resulting in a faster rate.

Hydrophobic Patterns. Hydrophobic patterning is one of the most significant (p<0.001) determinants of aggregation rates in Eq (3). The importance of hydrophobic-hydrophilic patterns has been extensively studied by Hecht and co-workers [see, for example, Wurth, C., N. K. Guimard, and M. H. Hecht, *Mutations that reduce aggregation of the Alzheimer's Abeta42 peptide: an unbiased search for the sequence determinants of Abeta amyloidogenesis.* J Mol Biol, 2002. 319(5): p. 1279-90], and alternating patterns of the type that we used have been shown to be among the least common features of natural protein sequences [Broome, B. M. and M. H. Hecht, *Nature disfavors sequences of alternating polar and nonpolar amino acids: implications for amyloidogenesis.* J Mol Biol, 2000. 296(4): p. 961-8]. A length of five consecutive hydrophobic and hydrophilic alternating residues was found to yield the most significant correlation with aggregation kinetics. The positive value of the coefficient for patterns (0.96) indicates that the more patterns of this type in a given sequence, the faster the aggregation rate.

Secondary Structure Propensities. The significance and signs of the coefficients for α-helical (p=0.057, $α_α$=−0.07) and β-sheet (p=0.031, $α_β$=0.08) propensities indicate, as expected, that the formation of amyloid fibrils is favoured by a high value of the overall β-sheet propensity and by a low value of the overall α-helical propensity in the polypeptide sequence.

Charge. The highly significant (p<0.001) negative sign for the coefficient of the charge contribution (α=−0.47) indicates that the aggregation rate increases as the absolute value of the net charge decreases; such a correlation has been noted before for AcP and its mutants [Chiti, F., et al., *Studies of the aggregation of mutant proteins in vitro provide insights into the genetics of amyloid diseases.* Proc Natl Acad Sci USA, 2002b. 99 Suppl 4: p. 16419-26]. In one study, however, charges of +1 were shown to be more favourable to amyloid formation than net charges of 0 or ±2 [Lopez De La Paz, M., et al., *De novo designed peptide-based amyloid fibrils.* Proc Natl Acad Sci USA, 2002. 99(25): p. 16052-7]. However, modifications of the functional form of $I^{ch}$, the term describing the contribution of charge to the aggregation rates in Eq (3), from a linear form to a polynomial one with maxima at ±1 gave a lower correlation coefficient. It is likely, that conditions favouring fast aggregation kinetics do not necessarily coincide with those optimal for the formation of well ordered amyloid assemblies, as suggested in some experimental systems analysed so far. In this way if we examine the parameters important for influencing the aggregation kinetics of a given polypeptide regardless of the particular morphological characteristics exhibited by the final assemblies, our findings are consistent with previous results [Chiti ibid], suggesting that accumulation of charges exert an inhibitory effect on polypeptide aggregation, no mater what the final structure adopted by the polypeptide is.

Extrinsic Factors pH. Our results indicate that the pH is inversely related to aggregation rates. This is consistent with the observation that formation of amyloid fibrils is often found to occur at low pH. The pH is less significant (p=0.28) than the other factors in Eq (3), most likely because it is to a large extent already accounted for by other factors, such the hydrophobicity, hydrophobic patterns, and charge.

Ionic Strength. We found a highly significant (p<0.001) correlation in the data between higher ionic strengths and slower aggregation rates. If the ionic strength is left out of the analysis, Eq (3) still yields a correlation coefficient of 0.87 rather than 0.92 between the calculated and observed aggregation rates. Increased ionic strength may, at least in some cases, decrease aggregation rates over the ranges of values used in our dataset.

Peptide Concentration. According to Eq (3), the rate of aggregation increases significantly (p<0.001) with the peptide concentration C. We tested several functional forms of $E^{conc}$, and the logarithmic dependence, $E^{conc}=\ln(C+1)$ allowed for the best predictions over a wide range of C. Since all the experimental data that we considered were obtained above the critical concentration for aggregation, the extrapolation of the results obtained with Eq (3) to low C should be considered with care.

Additional Factors to be Considered and Future Improvements

The present analysis relies in a somewhat limited amount of experimental data available to date, and as a result elements relevant to define in detail polypeptide aggregation could have been overlooked due to the absence of data. An alternative approach could use neural networks to extract parameters, without the need of make assumptions on the (unknown) functional form [Rumelhart, D. and J. McClellard, *Parallel Distributed Processing: Exploration in the Microstructure of Cognition*. MIT Press, Cambridge, Mass., 1986], however this approach would be less informative in terms of understanding the relative importance of different elements in the mechanism of polypeptide aggregation.

We have considered here a collection of intrinsic and extrinsic factors contributing to the aggregational behaviour of polypeptides. Additional factors, such as stability of the native state, temperature or stirring can be included in the prediction algorithm, provided that suitable data are available to enable a reliable determination of their coefficients. An increased temperature is known to lead to faster aggregation rates in many cases. However, the lack of variation among the experimental temperatures for the rates included in the dataset made it difficult to establish accurately its contribution. Another important experimental factor influencing the kinetics of aggregation is the extent to which solutions are agitated or 'stirred.' If the effects of stirring were defined then this factor could potentially be included in equation 3. As mentioned, the above described procedure does not take into account the stability of the native state, but rather predicts rates of aggregation from a destabilized state. In principle, however, the stability of the native state could also be considered as an additional factor in the formula.

Using a combination of intrinsic and extrinsic parameters as detailed above together with a multivariate analysis of the available experimental data, equation (3) is able to predict absolute aggregation rates for any polypeptide sequence. The aggregation rates calculated using our approach correlate to the experimentally observed rates with a coefficient of 0.92 (bootstrap cross-validated 0.84, jackknife cross-validated 0.88) and can, therefore, be expected to produce accurate predictions within the ranges of condition included in our dataset, namely pH 4.4 to 9.0, ionic strength of 0.1 to 150 mM, and peptide concentration of 0.01 to 2 mM. The formula derived in this example was obtained by ignoring the fact that certain regions of a polypeptide chain are more important than others for determining the aggregation rates. This approximation is probably responsible for the relatively small influence of secondary structure propensities that we found in the example. Nonetheless we have found a highly significant correlation between predicted and experimental aggregation rates. The quality of the prediction may be improved further by combining the equation (3) with an algorithm capable of predicting the sensitive regions of a polypeptide chain, such as that described above with reference to Example 6. However, the fact that sensitive regions important for aggregation do not need to be known to use this formula greatly enhances its general applicability.

Thus we have analysed the effect of a combination of intrinsic properties of the sequence and extrinsic experimental elements to accurately predict the aggregation rates exhibited by different polypeptides of different origin. The remarkable agreement between the predicted absolute aggregation rates and the experimentally obtained values shows that simple parameters defining a polypeptide sequence and its environment can be used to rationalize, to a large extent, its aggregation propensity. The ability to predict the aggregation propensity exhibited by a given peptide or protein with accuracy and precision that is potentially a powerful tool to assist in understanding the behaviour of natural polypeptides and their propensity to aggregate, as well as to establish how sequences have evolved in nature to avoid misfolding. Moreover, this approach may be applied to better understanding and perhaps even predict the onset of amyloidoses and other depositional diseases, as well as helping to explore effective therapeutic strategies for their treatment.

Datasets

Kinetic data on the aggregation of AcP and its mutants were obtained from the literature as set out under Table 8; in these studies ThT (Thioflavin T) fluorescence was used to determine the rate of aggregation of each protein in solution. AcP data were all measured under identical conditions and provided the largest set of data used in the present analysis (60 sequences). The second set of data included the aggregation rates of several different peptides under different conditions, obtained from published results (see Table 8 for references). A literature search was initially conducted using 'kinetics' and 'fibril' or 'amyloid' as keywords, resulting in an initial list of over 800 references. We then selected a set of readily-available studies that described kinetic experiments on short peptides or proteins in a buffer solution that formed electron microscope-detectable fibrils over the course of the experiment. We thus chose ten references that provided us with kinetic data on 23 sequences under different salt concentrations, occasionally with small amounts of co-solvent remaining from the peptide stock solution. Once chosen using the criteria described above, no sequences were excluded from the analysis, nor were new ones added.

Aggregation rates were determined from kinetic traces obtained by the following methods: ThT (Transthyretin) fluorescence, turbidity, CD, or direct estimation of the relative amount of aggregated material using techniques such as sedimentation, size exclusion chromatography, and filtration. Although these methods detect slightly different aggregation aspects, they are closely linked, and in some systems where two or more experimental techniques have been applied, a similar kinetic profile has been observed. Lag phases were not considered in our analysis, because they were often not reported or difficult to extract from the published data. Moreover, a comprehensive understanding of lag phases in protein aggregation is still lacking, and the present analysis focuses on the aggregation kinetics after the lag phase, where an elongation phase with single exponential behaviour is generally observed. Kinetic traces were fitted to the equation $y=A(1-e^{-kx})$ where k is the rate constant in $s^{-1}$. The natural logarithm of the rate constant ($\ln(k)$) was used in Eq (3), since the values of $\ln(k)$ were better described by a normal distribution than k itself. In some systems, seeded and non-seeded solutions result in nearly identical aggregation rates if the lag phase in the non-seeded solution is disregarded. We estimated that an inclusion of the lag phase would change the aggregation rates by no more than a factor of five, resulting in an error of 1.6 in the logarithm; this number should be compared with the statistical error of 0.7 on our predictions.

The values of $\ln(k)$ determined by different methods in these papers differ by less than 0.2 units in all but one case, where turbidity kinetics and ThT kinetics differ by 1.9 units, probably as a result of other differences in experimental procedure. In the experimental studies that we considered, mass/volume analyses were used in the absence of an independent technique to confirm the results. However, since these methods may be considered the most direct method of observing the growth of physical aggregates, the data obtained solely by these methods were included in the analysis.

Derivation of the Formula

The functional form of each factor in Eq (3) was chosen after examining a variety of phenomenological combinations of the factors likely to influence the propensity to aggregate. We considered two classes of factors, intrinsic and extrinsic. Intrinsic factors included properties of the amino acid sequence, such as hydrophobicity, hydrophobic patterns, secondary structure propensities, and charge. Their functional forms were determined by examining a subset of AcP mutants to find the representation that best correlated with changes in ln(k) amongst the mutants. The extrinsic factors included peptide concentration, ionic strength, and pH. We used a logarithm form for the term describing the effect of the peptide concentration in order to avoid overestimating rates at higher concentrations. The other terms were assumed to have a linear form.

Regressions were carried out using the statistical software Rweb1.03 [Rweb1.03, www.math.montana.edu The R Development Core Team Version 1.4.1, 2002] to obtain coefficients $\alpha$ in Eq (3) that minimize the differences between the calculated and experimental ln(k) values. In interpreting the meaning of the numerical constants in the formula we should note its phenomenological nature. The formula may contain double-counting for some factors (e.g. hydrophobicity and hydrophobic patterns), but this is not problematic as the coefficients are fitted from experimental data and not derived from first principles.

Flow Chart for a Computer Implementation of the Methods of Example 7

Figure 13:
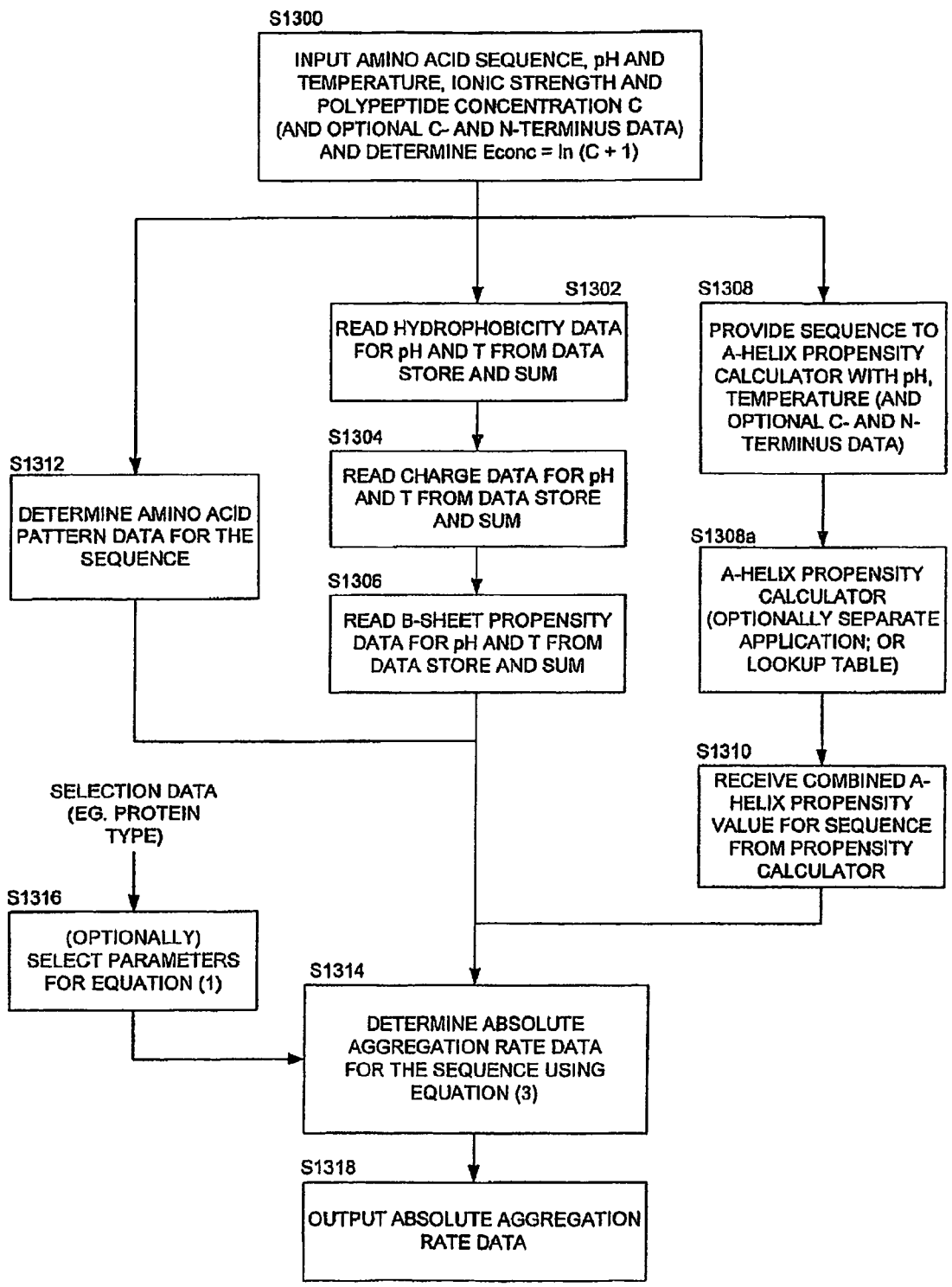
FIG. 13 shows a flow chart of a procedure according to an embodiment of the present invention for determining an estimate of an absolute aggregation rate of a polypeptide.

FIG. 13 shows a further procedure, which again may be implemented using the computer system of FIG. 3 running appropriate code, for implementing equation 3 above to determine an estimate of an absolute aggregation rate rather than the relative aggregation rates predicted by equations 1 and 2.

Many of the steps of FIG. 13 are similar to those of FIG. 6 above and, in particular, steps s1300-s1312, and s1316 broadly correspond to steps s600-s612, and s616 of FIG. 6. However at step s1300, in addition to the parameters of step s600, further extrinsic parameters are input to the procedure, in particular an ionic strength value (of the polypeptide solution, for example in millimolar units), and a concentration value C which is a measure of polypeptide concentration, for example in millimolar units, and which is used to determine a concentration parameter $E^{conc}$ for equation 3 using $E^{conc}=\ln(C+1)$. These additional extrinsic values are used in determining the absolute aggregation rate using equation 3 at step s1314. At steps s1302 to s1306 hydrophobicity, charge and $\beta$-sheet propensity data are summed (in a similar manner to the FIG. 4 procedure) rather than determined for each amino acid. At step s1312 each alternating pattern of amino acids identified when stepping through the sequence is given a value of, say, +1 rather than assigning a value of $I^{pat}$ to each particular amino acid of the sequence. At step s1318 the absolute aggregation rate data is output in any conventional manner for further use, for example as previously described.

REFERENCES

Dobson, C. M. Protein folding and its links with human disease. *Biochem. Soc. Symp.* 68, 1-26 (2001).

Jarrett, J. T., Berger, E. P. & Lansbury, P. T. Jr. The carboxy terminus of the beta amyloid protein is critical for the seeding of amyloid formation: implications for the pathogenesis of Alzheimer's disease. *Biochemistry* 32, 4693-4697.

Selkoe, D. J. Alzheimer's disease: genes, proteins, and therapy. *Physiol. Rev.* 81, 741-766 (2001).

Siepen, J. A. & Westhead, D. R. The fibril_one on-line database: Mutations, experimental conditions, and trends associated with amyloid fibril formation. Protein Sci. 11, 1862-1866 (2002).

Volles, M. J. & Lansbury, P. T. Jr. Vesicle permeabilization by protofibrillar $\alpha$-synuclein is sensitive to Parkinson's disease-linked mutations and occurs by a pore-like mechanism. *Biochemistry,* 41, 4595-4602 (2002).

For the following references the numbers are those used in table 2:

11. Azriel, R. & Gazit, E. Analysis of the minimal amyloid-forming fragment of the islet amyloid polypeptide. An experimental support for the key role of the phenylalanine residue in amyloid formation. *J. Biol. Chem.* 276, 34156-34161 (2001).

12. Sakagashira, S., Hiddinga, H. J., Tateishi, K., Sanke, T., Hanabusa, T., Nanjo, K. & Eberhardt, N. L. S20G mutant amylin exhibits increased in vitro amyloidogenicity and increased intracellular cytotoxicity compared to wild-type amylin. *Am. J. Pathol.* 157, 2101-2109 (2000).

13. Salmona, M., Malesani, P., De Gioia, L., Gorla, S., Bruschi, M., Molinari, A., Della Vedova, F., Pedrotti, B., Marrari, M. A., Awan, T., Bugiani, O., Forloni, G., Tagliavini, F. Molecular determinants of the physicochemical properties of a critical prion protein region comprising residues 106-126. *Biochem J.* 342, 207-214 (1999).

14. Thompson, A. J., Barnham, K. J., Norton, R. S., Barrow, C. J. The Val-210-Ile pathogenic Creutzfeldt-Jakob disease mutation increases both the helical and aggregation propensities of a sequence corresponding to helix-3 of PrP(C). Biochim. Biophys. Acta. 1544, 242-254 (2001).

15. Conway, K. A., Lee, S. J., Rochet, J. C., Ding, T. T., Williamson, R. E. & Lansbury, P. T. Jr. (2000). Acceleration of oligomerization, not fibrillization, is a shared property of both alpha-synuclein mutations linked to early-onset Parkinson's disease: implications for pathogenesis and therapy. *Proc. Natl. Acad. Sci. USA,* 97, 571-576.

16. Giasson, B. I., Murray, I. V., Trojanowski, J. Q. & Lee, V. M. A hydrophobic stretch of 12 amino acid residues in the middle of $\alpha$-synuclein is essential for filament assembly. *J. Biol. Chem.* 276, 2380-2386 (2001).

17. Van Nostrand, W. E., Melchor, J. P., Cho, H. S., Greenberg, S. M. & Rebeck, G. W. (2001). Pathogenic effects of D23N Iowa mutant amyloid beta-protein. *J. Biol. Chem.* 276, 32860-32866.

18. Miravalle L, Tokuda T, Chiarle R, Giaccone G, Bugiani O, Tagliavini F, Frangione B, Ghiso J. J Biol Chem 2000 Sep. 1; 275(35):27110-6

19. Nilsberth, C., Westlind-Danielsson, A., Eckman, C. B., Condron, M. M., Axelman, K., Forsell, C., Stenh, C., Luthman, J., Teplow, D. B., Younkin, S. G., Naslund, J. & Lannfelt, L. (2001). The 'Arctic' APP mutation (E693G) causes Alzheimer's disease by enhanced A$\beta$ protofibril formation. *Nature Neurosci.* 4, 887-893.

20. Esler, W. P., Stimson, E. R., Ghilardi, J. R., Lu, Y. A., Felix, A. M., Vinters, H. V., Mantyh, P. W., Lee, J. P. & Maggio, J. E. Point substitution in the central hydrophobic cluster of a human β-amyloid congener disrupts peptide folding and abolishes plaque competence. Biochemistry, 35, 13914-13921 (1996).

21. Barghorn, S., Zheng-Fischhofer, Q., Ackmann, M., Biemat, J., von Bergen, M., Mandelkow, E. M. & Mandelkow, E. (2000). Structure, microtubule interactions, and paired helical filament aggregation by tau mutants of frontotemporal dementias. *Biochemistry,* 39, 11714-11721.

22. Gamblin, T. C., King, M. E., Dawson, H., Vitek, M. P., Kuret, J., Berry, R. W., Binder, L. I. In vitro polymerization of tau protein monitored by laser light scattering: method and application to the study of FTDP-17 mutants. *Biochemistry,* 39, 6136-6144 (2000).

23. Nacharaju, P., Lewis, J., Easson, C., Yen, S., Hackett, J., Hutton, M. & Yen, S. H. Accelerated filament formation from tau protein with specific FTDP-17 missense mutations. *FEBS Lett.* 447, 195-199 (1999).

23b. Li, L., Von Bergen, M., Mandelkow, E. M. & Mandelkow, E. Structure, stability, and aggregation of paired helical filaments from tau protein and FTDP-17 mutants probed by tryptophan scanning mutagenesis. *J. Biol. Chem*. in press (2002).

24. Symmons, M. F., Buchanan, S. G., Clarke, D. T., Jones, G. & Gay, N. J. X-ray diffraction and far-UV CD studies of filaments formed by a leucine-rich repeat peptide: structural similarity to the amyloid fibrils of prions and Alzheimer's disease β-protein. *FEBS Lett.* 412, 397-403 (1997).

25. Orpiszewski, J. & Benson, M. D. Induction of beta-sheet structure in amyloidogenic peptides by neutralization of aspartate: a model for amyloid nucleation. *J. Mol. Biol.* 289, 413428 (1999).

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

The invention claimed is:

1. A method for predicting a part of an amino acid sequence, the method comprising using sufficiently programmed computer for profiling an amino acid sequence to identify a part of said amino acid sequence which is predicted to promotes aggregation of a polypeptide defined by said sequence, the method comprising:
    determining aggregation propensities for a plurality of parts of said sequence to determine an aggregation propensity profile for said sequence;
    comparing said aggregation propensities of said aggregation propensity profile to determine one or more parts of said sequence which are predicted to promote aggregation;
    wherein said determining comprises determining, for each of a plurality of amino acids of said sequence, a hydrophobicity value, at least one of an α-helix propensity value and β-sheet propensity value, a charge value, and a pattern value representing a pattern of at least one of hydrophilic and hydrophobic amino acids in the vicinity of each said amino acid, multiplying each of said values by a scaling factor, and summing said scaled values to determine said aggregation propensities; and
    outputting a result to at least one of a memory and a display device.

2. A method as claimed in claim 1, wherein said determining comprises determining a pattern value representing a pattern of alternating hydrophilic and hydrophobic amino acids.

3. A method as claimed in claim 2 wherein said determining comprises determining on a pattern having a length of at least five amino acids.

4. A method as claimed in claim 1 further comprising modifying said amino acid sequence and repeating said aggregation propensity determining to identify one or more parts of said sequence which are predicted to promote aggregation.

5. A method as claimed in claim 4 wherein said modifying comprises, for each of a plurality of positions in said amino acid sequence, selecting each of a plurality of alternative amino acids for said repeated propensity determining.

6. A method as claimed in claim 4 further comprising comparing said repeatedly determined aggregation propensities to identify one or more parts of said sequence which are predicted to promote aggregation.

7. Computer program code stored on a machine readable media to, when running, predict a part of an amino acid sequence which is predicted to promote aggregation of a polypeptide associated with the sequence, the code comprising code to:
    determine aggregation propensities for a plurality of parts of said sequence to determine an aggregation propensity profile for said sequence;
    compare said aggregate propensities of said aggregation propensity profile to determine one or more parts of said sequence which are predicted to promote aggregation; and
    wherein said code to determine comprises code to determine, for each of a plurality of amino acids of said sequence, a hydrophobicity value, at least one of an α-helix propensity value and β-sheet propensity value, a charge value, and a pattern value representing a pattern of at least one of hydrophilic and hydrophobic amino acids in the vicinity of each said amino acid, to multiply each of said values by a scaling factor, and to sum said scaled values to determine said aggregation propensities.

8. A computer system for predicting a part of an amino acid sequence which promotes aggregation of a polypeptide associated with the sequence, the computer system comprising:
    a data store for storing each of a plurality of amino acids of said sequence, a hydrophobicity value, at least one of an α-helix propensity value and a β-sheet propensity value, and a charge value,
    a program store storing processor implementable code; and
    a processor, coupled to said program store and to said data store for implementing said stored code, the code comprising code for controlling the processor to:
    input said amino acid sequence;
    read, for each of a plurality of amino acids of said sequence, a said hydrophobicity value, at least one of said α-helix propensity value and said β-sheet propensity value, and a said charge value from said data store;
    determine aggregation propensity data for a plurality of parts of said sequence from said hydrophobicity, at least one of α-helix and β-sheet propensity, and charge values and from a pattern value dependent upon a pattern of at least one of hydrophilic and hydrophobic amino acids in said sequence, to determine an aggregation propensity profile for said sequence; and output said aggregation propensity profile for identifying a part of said sequence which is predicted to promote aggregation of a polypeptide associated with the sequence.

9. A computer system as claimed in claim 8 further comprising a web server.

10. The method of claim 1, wherein said determining comprises determining an aggregation propensity for each amino acid of said amino acid sequence.

* * * * *